(12) United States Patent
Yen et al.

(10) Patent No.: US 10,035,806 B2
(45) Date of Patent: Jul. 31, 2018

(54) DERIVATIZED CORROLES AND METALLOCORROLES AND THEIR USE AS IMAGING AND THERAPEUTIC AGENTS

(71) Applicant: CALIFORNIA INSTITUTE OF TECHNOLOGY, Pasadena, CA (US)

(72) Inventors: Melanie A. Yen, Pasadena, CA (US); Harry B. Gray, Pasadena, CA (US); Robert H. Grubbs, South Pasadena, CA (US); Joshua Palmer, Pasadena, CA (US)

(73) Assignee: California Institute of Technology, Pasadena, CA (US)

(*) Notice: Subject to any disclaimer, the term of this patent is extended or adjusted under 35 U.S.C. 154(b) by 0 days.

(21) Appl. No.: 15/286,983

(22) Filed: Oct. 6, 2016

(65) Prior Publication Data

US 2017/0096434 A1    Apr. 6, 2017

Related U.S. Application Data

(60) Provisional application No. 62/237,997, filed on Oct. 6, 2015.

(51) Int. Cl.
*C07D 487/22* (2006.01)
*A61K 31/409* (2006.01)
*C07F 5/00* (2006.01)

(52) U.S. Cl.
CPC ............ *C07D 487/22* (2013.01); *C07F 5/003* (2013.01)

(58) Field of Classification Search
CPC .................................................. C07D 487/22
See application file for complete search history.

(56) References Cited

U.S. PATENT DOCUMENTS

| | | | |
|---|---|---|---|
| 4,649,151 A | 3/1987 | Dougherty et al. |
| 5,171,749 A | 12/1992 | Levy et al. |
| 5,198,460 A | 3/1993 | Pandey et al. |
| 5,225,433 A | 7/1993 | Dougherty et al. |
| 5,399,583 A | 3/1995 | Levy et al. |
| 5,459,159 A | 10/1995 | Pandey et al. |
| 5,489,590 A | 2/1996 | Gulliya et al. |
| 5,563,132 A | 10/1996 | Bodaness |
| 6,462,192 B2 | 10/2002 | Robinson et al. |
| 6,541,628 B1 | 4/2003 | Gross et al. |
| 6,730,666 B1 | 5/2004 | Yayon et al. |
| 6,827,926 B2 | 12/2004 | Robinson et al. |
| 6,939,963 B2 | 9/2005 | Gross et al. |
| 8,680,266 B2 | 3/2014 | Palmer et al. |
| 8,791,099 B2 | 7/2014 | Gross et al. |

OTHER PUBLICATIONS

Cellular uptake and anticancer activity of carboxylated gallium corroles. Pribisko et al. (PNAS, 2016, E2258-E2266).*

Agadjanian et al., "Specific delivery of corroles to cells via noncovalent conjugates with viral proteins", Pharmaceutical Research, 2006, 23(2), 367-377.
Agadjanian et al., "Tumor detection and elimination by a targeted gallium corrole", Proceedings of the national Academy of Sciences USA, 2009, 106(15), 6105-6110.
Alemayehu et al., "Gold Corroles", Journal of Porphyrins and Phthalocyanines, 2011, 15(02), 106-110.
Aviezer et al., "Porphyrin analogues as novel antagonists of fibroblast growth factor and vascular endotheilial growth factor receptor binding that inhibit endothelial cell proliferation, tumor progression, and metastasis", Cancer Research, 2000, 60(11), 2973-2980.
Aviv et al., "Corrole-based applications", Chem Commun, 2007, 20, 1987-1999.

(Continued)

*Primary Examiner* — Brian E McDowell
(74) *Attorney, Agent, or Firm* — Baker & Hostetler LLP

(57) ABSTRACT

The present invention is directed to derivatized corroles, methods of making and using the same as imaging and therapeutic agents. In certain embodiments, the corroles are compounds having a Structure (I-H) and (I-M):

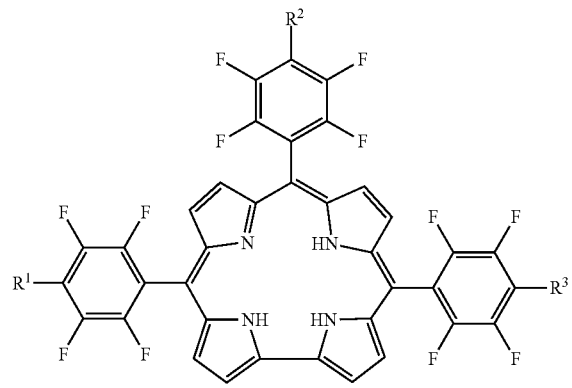

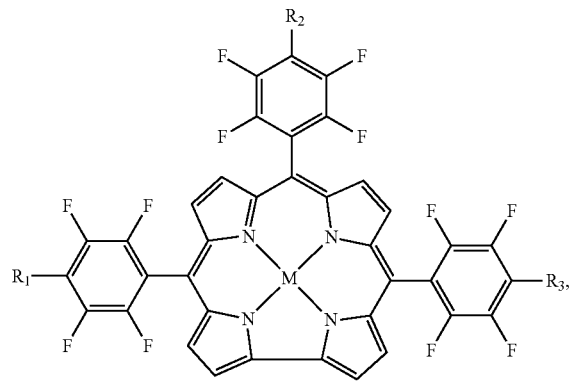

where $R^1$, $R^2$, $R^3$, and $R^4$ are independently —F or —N(H)—$(CH_2)_m$—Y, provided that at least one of $R^1$, $R^2$, $R^3$, and $R^4$ is —N(H)—$(CH_2)_m$—Y, and m and Y are described herein.

15 Claims, 12 Drawing Sheets

(56) References Cited

OTHER PUBLICATIONS

Aviv-Harel et al., "Aura of Corroles", Chemistry, 2009, 15(34), 8382-8394.
Aviv-Harel et al., "Coordination chemistry of corroles with focus on main group elements", Coordination Chemistry Reviews, 2011, 255, 717-736.
Bendix et al., "Structure, electrochemical, and photophysical properties of gallium(III) 5,10,15-tris(pentafluorophenyl)corrole", 2000, Angewandt Chemie, 39(22), 4048-4051.
Berenbaum, M.C., "In vivo determination of the fractional kill of human tumor cells by chemotherapeutic agents", Cancer Chemotherapy Reports, 1972, 56(5), 563-571.
Bickerton et al., "Quantifying the chemical beauty of drugs", Nat Chem, 2012, 4(2), 90-98.
Blumenfeld et al., "Control of oligomerization and oxidation steps in the synthesis of tris(pentafluorophenyl)corrole", European Journal of Organic Chemistry, 2015, 14, 3022-3025.
Chitambar et al., "Development of gallium compounds for treatment of lymphoma: Gallium maltolate, a novel hydroxypyrone gallium compound, induces apoptosis and circumvents lymphoma cell resistance to gallium nitrate", The Journal of Pharmacology and Experimental Therapeutics, 2007, 322(3), 1228-1326.
Chua et al., "Gallium maltolate is a promising chemotherapeutic agent for the treatment of hepatocellular carcinoma", Anticancer Research, 2006, 26(3A), 1739-1743.
Collins, J.M., "The NCI Developmental Therapeutic Program", Clinical Advances in Hematology & Oncology, 2006, 4(4), 271-273.
Driggers et al., "The exploration of macrocycles for drug discovery—an underexploited structural class", Nature Reviews Drug Discovery, 2008, 7(7), 608-624.
Ethirajan et al., "The role of porphyrin chemistry in tumor imaging and photodynamic therapy", Chemical Society Reviews, 2011, 40(1), 340-362.
Fallahi-Sichani et al., "Metrics other than potency reveal systematic variation in response to cancer drugs", Nature Chemical Biology, 2013, 9(11), 708-714.
Giordanetto et al., "Macrocyclic drugs and clinical candidates: What can medicinal chemists learn from their properties?", Journal of Medicinal Chemistry, 2014, 57(2), 278-295.
Gross et al., "Solvent-free condensation of pyrrole and pentafluorobenzaldehyde: A novel synthetic pathway to corrole and oligopyrromethenes", Organic Letters, 1999, 1(4), 599-602.
Gross et al., "The first direct synthesis of corroles from pyrrole", Angewandte Chemie Internationation Edition, 1999, 38(10), 1427-1429.
Gryko D.T., "A simple, rational synthesis of meso-substituted $A_2B$-corroles", Chemical Communications, 2000, 22(2000), 2243-2244.
Gryko D.T., "Recent advances in the synthesis of corroles and core-modified corroles", European Journal of Organic Chemistry, 2002, 2002(11), 1735-1743.
Gryko et al., "Adventures in the synthesis of meso-substituted corroles", Journal of Porphyrins and Phthalocyanines, 2008, 12(08), 906-917.
Guilard et al., "Synthesis of corroles bearing up to three different meso substitutents", Organic Letters, 2002, 4(25), 4491-4494.
Hori et al., "Nucleophilic substitution reactions of meso-5,10,15-tris(pentafluorophenyl)-corrole; synthesis of ABC-type corroles and corrole-based organogels", Eur J Org Chem, 2010, 12, 2379-2386.
Hwang et al., "A mechanistic study of tumor-targeted corrole toxicity", Molecular Pharmaceutics, 2011, 8(6), 2233-2243.
Johnson et al., "The synthesis of derivatives of corrole pentadehydrocorrin", Journal of the Chemical Society, 1960, 0 (1960), 1649-1653.
Johnson et al., "The synthesis of derivatives of corrole—amendment", Proceedings of the Chemical Society of London, 1961, 168-169.
Johnson et al., "The pentadehydrocorrin (corrole) ring system", Proceedings of the Chemical Society of London, 1964, 89-90.
Johnson et al., "Synthesis of corroles and related ring systems", Proceedings of the Roal Society A, Mathematical, Physical and Engineering Sciences, 1965, 288(1414), 334-341.
Kotz, J., "Bringing macrocycles full circle", SciBX, 2012, 5(4), 1-7.
Kowalska et al., "Ground- and excited-state dynamics of aluminum and gallium corroles", Inorganic Chemistry, 2009, 48(6), 2670-2676.
Levasseur et al., "Modeling of the time-dependency of in Vitro drug cytotoxicity and resistance", Cancer Research, 1998, 58(24), 5749-5761.
Licoccia et al., "Acid-catalyzed cyclization of 1,19-Unsubstituted a,c-Biladienes", The Journal of Organic Chemistry, 1998, 63(10), 3190-3195.
Lim et al., "Differential cytostatic and cytotoxic action of metallocorroles against human cancer cells: Potential platforms for anticancer drug development", Chemical Research in Toxicology, 2012, 25(2), 400-409.
Liu et al., "Photophysics of Soret-excited tetrapyrroles in solution. III. Porphyrin analogues: Aluminum and gallium corroles", 2008, Chemical Physics Letters, 459(1-6), 113-118.
Mitchison, T.J., "The proliferation rate paradox in antimitotic chemotherapy", Mol Biol Cell, 2012, 23(1), 1-6.
Monks et al., "Feasibility of a high-flux anticancer drug screen using a diverse panel of cultured human tumor cell lines", Journal of the National Cancer Institute, 1999, 83(11), 757-766.
Palmer, "Transition Metal Corrole Coordination Chemistry", Molecular Electronic Structures of Transition Metal Complexes I, vol. 142 of the series Structure and Bonding, Sep. 14, 2011, pp. 49-89.
Palmer et al., "Near-IR phosphorescence of iridium(III) corroles at ambient temperature", J Am Chem Soc, 2010, 132(27), 9230-9231.
Paolesse et al., "First direct synthesis of a corrole ring from a Monopyrrolic Precursor—Crystal and Molecular-Structure of (Triphenylphosphine)-(5,10,15-Triphenyl-2,3,7,8,12,13,17,18-Octamethylcorrolato)Cobalt(III)-Dichloromethane", Inorganic Chemistry, 1994, 33(6), 1171-1176.
Paolesse et al., "One-pot synthesis of corrolates by cobalt catalyzed cyclization of formylpyrroles", Inorganica Chimica Acta, 1996, 24(2), 55-66.
Paolesse et al., "5,10,15-Triphenylcorrole: A product from a modified Rothemund reaction", Chemical Communications, 1999, 1999(14), 1307-1308.
Paolesse et al., "Synthesis and Functionalization of meso-Aryl-Substituted Corroles", The Journal of Organic Chemistry, 2001, 66(2), 550-556.
Paolesse et al., "Corrole: The little big porphyrinoid", Synlett, 2008, 15, 2215-2230.
Pisarek et al., "Strategies toward the synthesis of amphiphilic porphyrins", Tetrahedron, 2014, 70(38), 6685-6715.
Pope et al., "Issues surrounding standard cytotoxicity testing for assessing activity of non-covalent DNA-binding metallo-drugs", Dalton Transactions, 2010, 39(11), 2772-2774.
Rabinovich et al., "Gold(I) and gold(III) corroles", Chemistry, 2011, 17(44), 12294-12301.
Richardson et al., "Two mechanisms of iron uptake from transferrin by melanoma cells. The effect of desferrioxamine and ferric ammonium citrate", The Journal of Biological Chemistry, 1992, 267(2), 13972-13979.
Richardson, D.R., "Iron and gallium increase iron update from transferrin by human melanoma cells: Further examination of the ferric ammonium citrate-activated iron update process", Biochimica et Biphysica Acta (BBA)—Molecular Basis of Disease, 2001, 1536(1), 43-54.
Saltsman et al., "Selective substitution of corroles: Nitration, hydroformylation, and chlorosulfonation", J Am Chem Soc, 2002, 124(25) 7411-7420.
Saltsman et al., "One-step conversions of a simple corrole into chiral and amphiphic derivatives", Tetrahedron Letters, 2003, 44(30), 5669-5673.
Shoemaker, R.H., The NCI60 human tumour cell line anticancer drug screen, Nature Reviews Cancer, 2006, 6(10), 813-823.

(56) References Cited

OTHER PUBLICATIONS

Sorasaenee et al., "Amphiphilic aluminum(III) and gallium(III) corroles", Journal of Porphyrins and Phtalocyanines, 2007, 11(03), 189-197.
Tang et al., "An in vitro enzymatic assay to measure transcription inhibition by gallium(III) and $H_3$ 5,10,15-tris(pentafluorophenyl)corroles" Journal of Visualized Experiments, 2015, 97, e52355, 8 pages.
Teo et al., "A cytocoxic and cytostatic gold(III) corrole", Chemical Communications, 2014, 50(89), 13789-13792.
Weaver et al., "Gallium(III) Corroles", Journal of Porphrynis and Phthalocyanines, 2004, 08(01), 76-81.
Yudin, A.K., "Macrocycles: Lessons from the distant past, recent developments, and future directions", Chem Sci, 2015, 6(1), 30-49.

\* cited by examiner

FIG. 4B
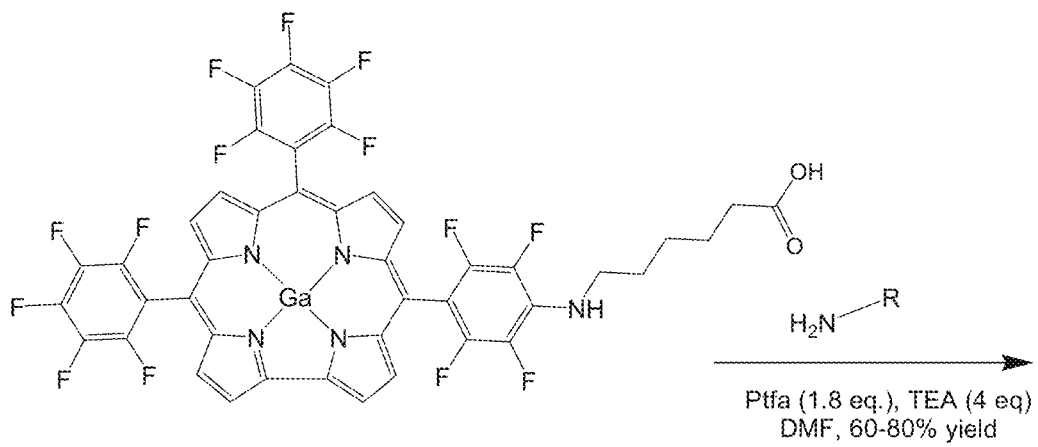
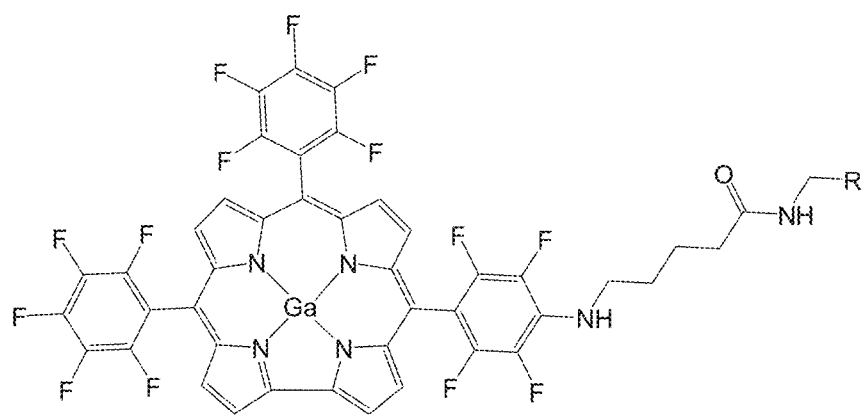
where R is:
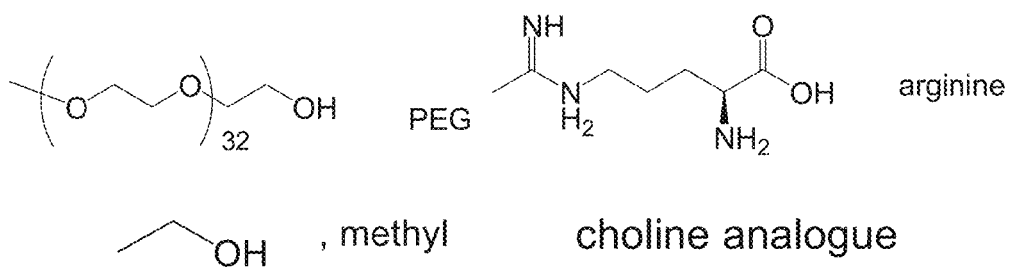

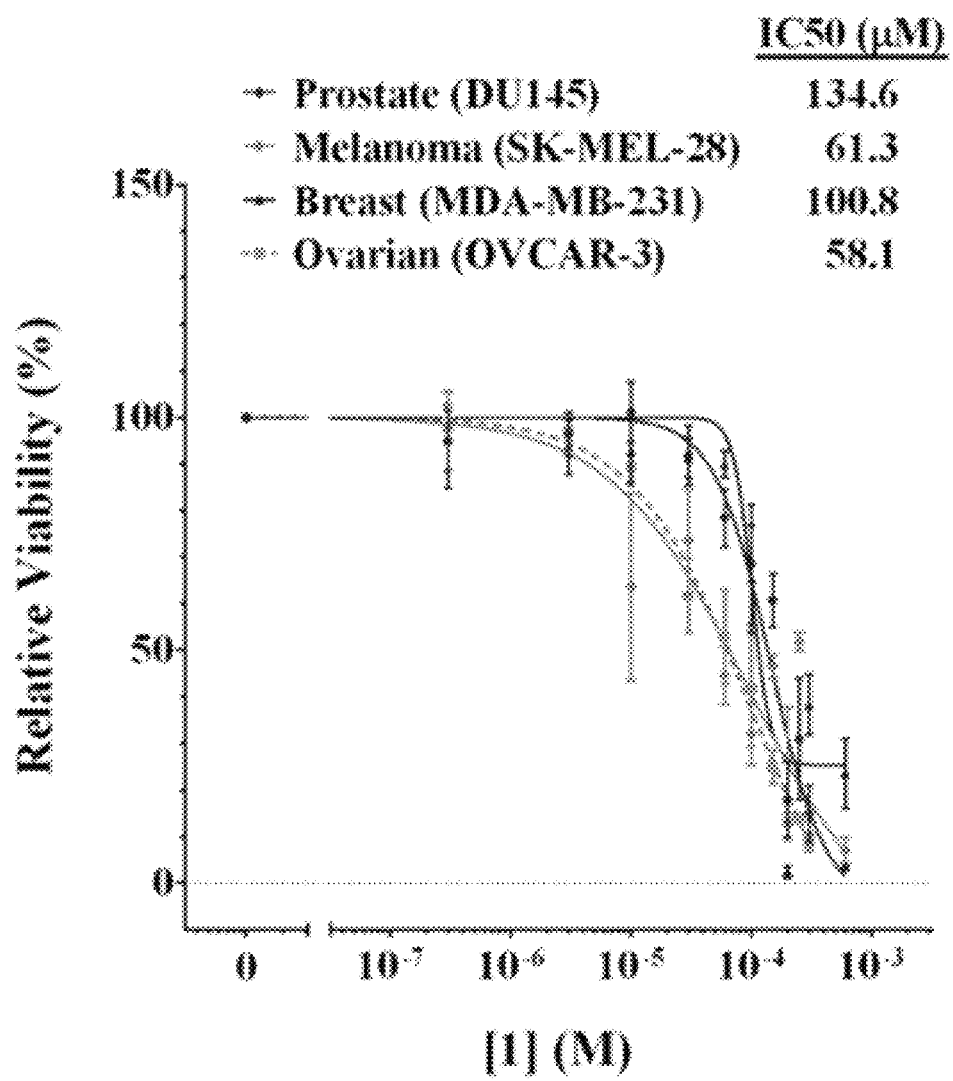
FIG. 6A: Complex 1

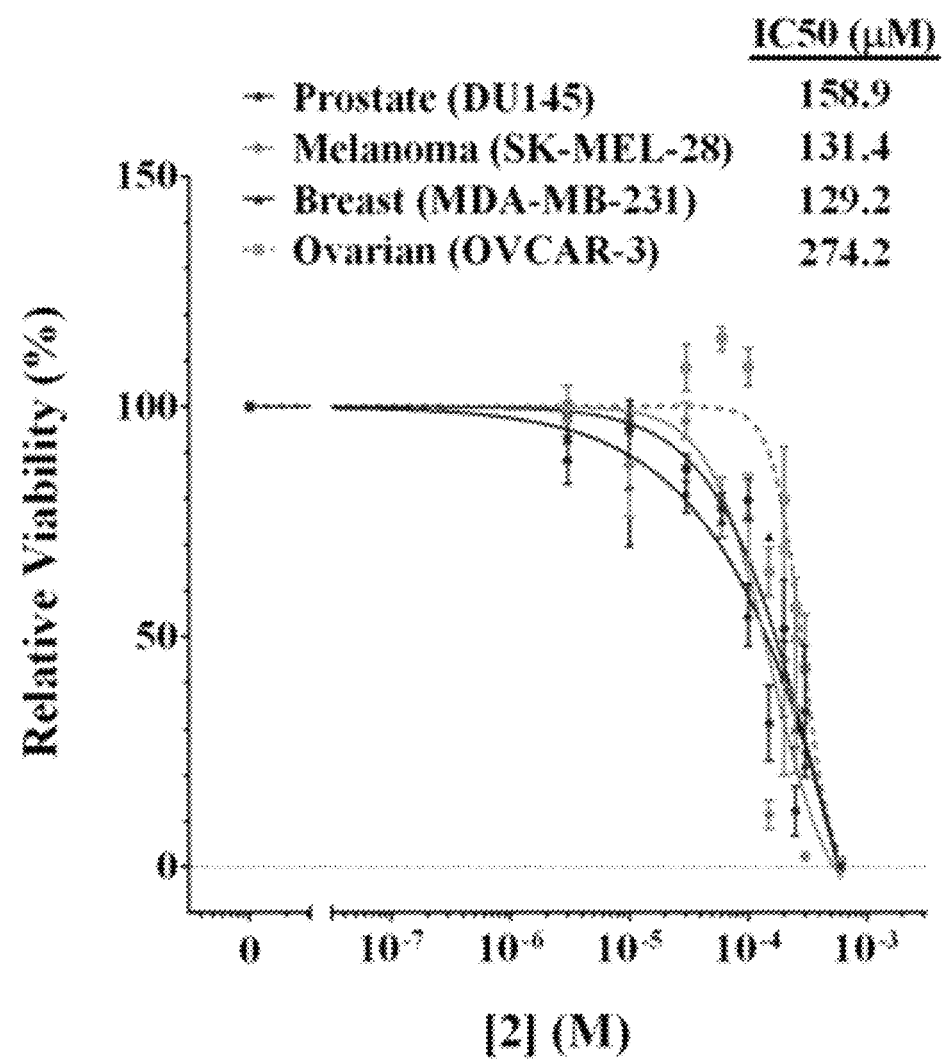
FIG. 6B: Complex 2

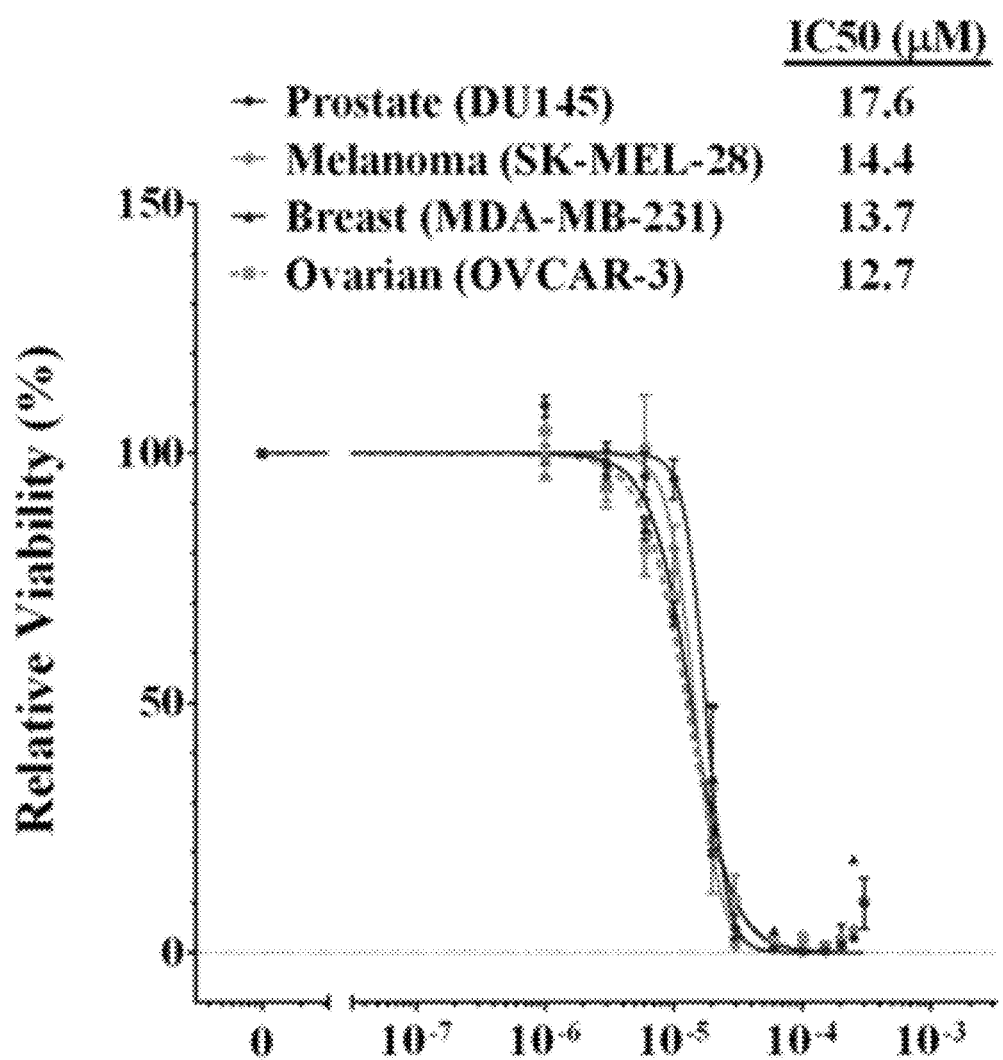
FIG. 6C: Complex 3

FIG. 6D: Complex 4
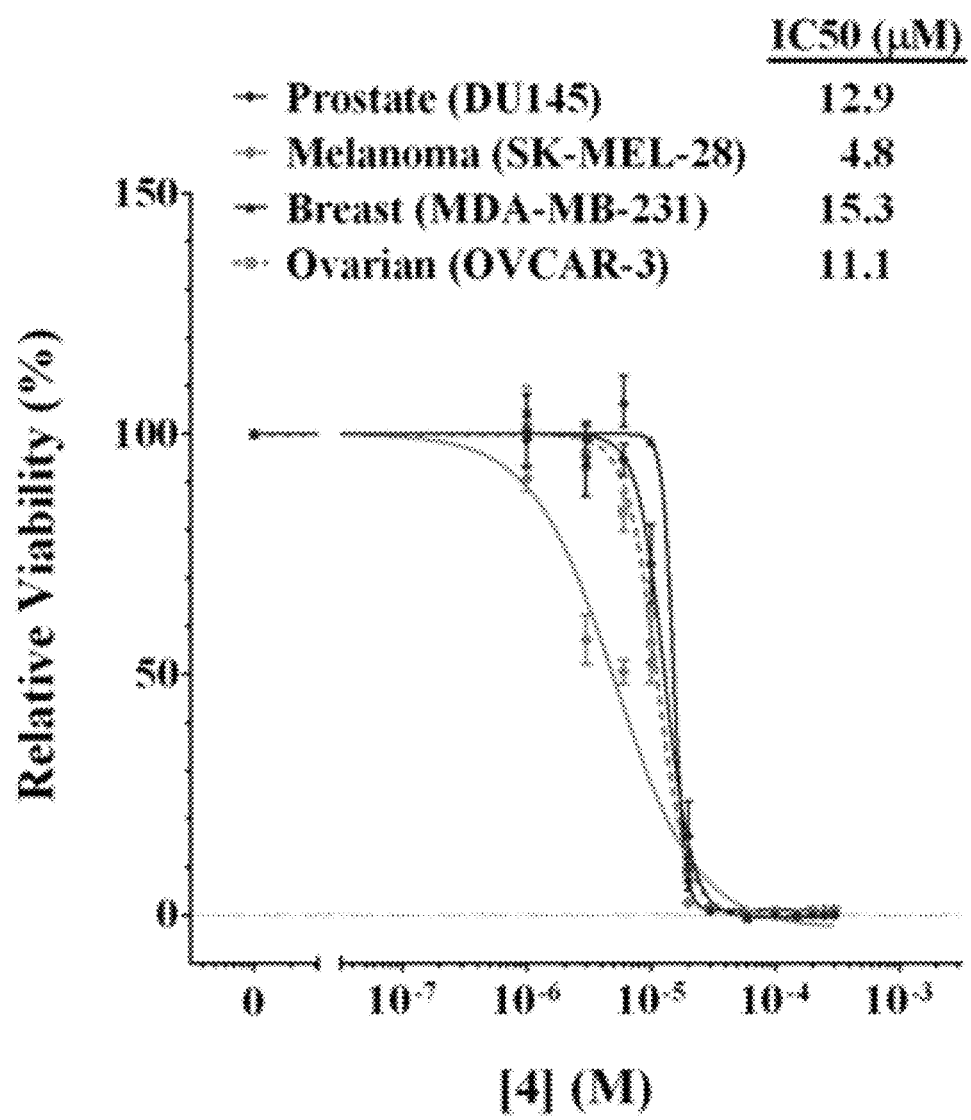

DERIVATIZED CORROLES AND METALLOCORROLES AND THEIR USE AS IMAGING AND THERAPEUTIC AGENTS

CROSS REFERENCE TO RELATED APPLICATIONS

This application claims priority to U.S. Patent Application Ser. No. 62/237,997, filed Oct. 6, 2015, the contents of which are incorporated by reference herein in its entirety for all purposes.

GOVERNMENT RIGHTS

This invention was made with government support under Grant No. DK019038 awarded by the National Institutes of Health. The government has certain rights in the invention.

TECHNICAL FIELD

The present invention is directed to derivatized corroles, methods of making and using the same as imaging and therapeutic agents.

BACKGROUND

Corroles are macrocyclic molecules related to porphyrins and other aromatic macrocycles whose pharmacological properties have led to the development of many drugs. The synthesis of analogs, determination of pharmacokinetics, targeting, and bioavailability represent significant challenges to the realize the full potential of these drugs, since it is not always clear as to the effect of various functionalizations on the inherent therapeutic properties of these macrocyclic compounds.

SUMMARY

The present invention is directed to uniquely derivatized corrole compounds, including metallocorroles, methods of making these derivatized corroles, and methods of using these derivatized corroles in the treatment of various diseases and conditions.

Certain embodiments comprise compound, including those of Formula (I-H), (I-M), (II-H), or (II-M):

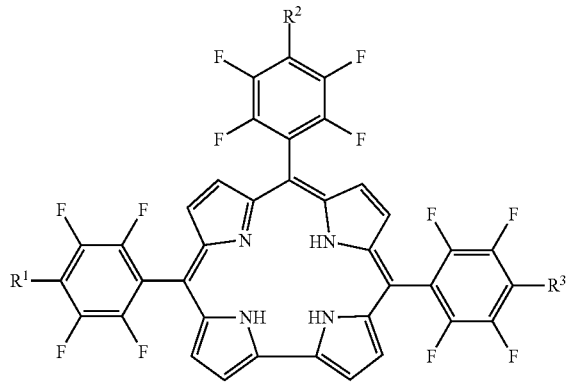
(I-H)

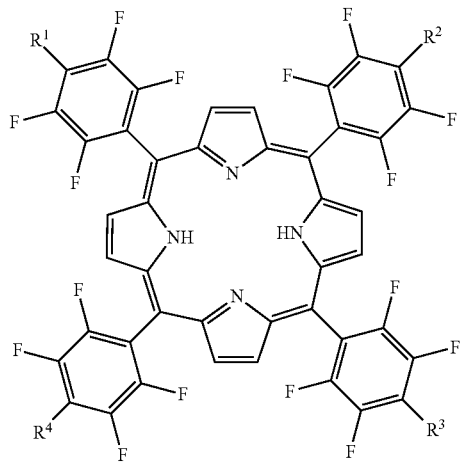
(II-H)

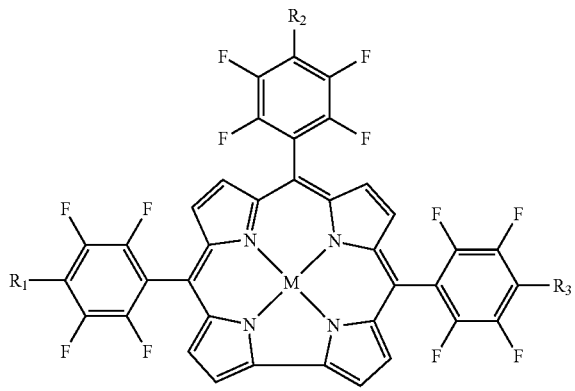
(I-M)

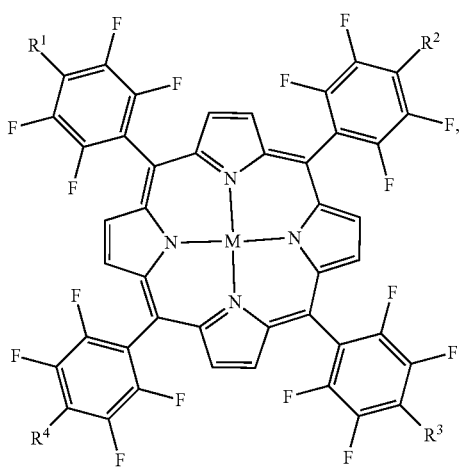
(II-M)

wherein
$R^1$, $R^2$, $R^3$, and $R^4$ are independently —F or —N(H)—$(CH_2)_m$—Y, provided that at least one of $R^1$, $R^2$, $R^3$, and $R^4$ is —N(H)—$(CH_2)_m$—Y;

—Y is —N(Z)$_2$, —O—Z, —C(O)—O—Z, —OC(O)Z—, —OC(O)O—Z, —C(O)N(Z)$_2$, —NH—C(O)—Z, —C(O)NHNH—Z

—Z is independently $R^5$, —$(CH_2)_m$—X, —$(CH_2)_m$—OR$^5$, —$(CH_2)_m$—SR$^5$, —$(CH_2)_m$—N(R$^5$)$_2$, —$(CH_2CH_2O)_n$—OR$^5$, —$(CH_2CH_2O)_n$—N(R$^5$)$_2$, —$(CH_2)_m$—N$_3$, —$(CH_2)_m$—C≡C—R$^5$, an amino acid, peptide, protein, polyol;

$R^5$ is independently H or $C_{1-12}$alkyl;

X is Cl, Br, or I;

m is independently 1-18 (preferably 1-12 or 1-6 or 1-2);

n is 1-32; and

M is Ag, Al, Co, Cr, Cu, Fe, Ga, Ge, Hf, Ir, Mo, Mn, Nb, Ni, Os, Pt, Re, Rh, Ru, Sb, Sn, Ta, Ti, V, or W, a lanthanide or actinide, or an isotope or radionuclide thereof, each of which is optionally coordinated to one or more axial ligands.

In some embodiments, one or more of the macrocyclic ring pyrroles may be substituted with carboxylic acid or sulfonate moieties, for example, as shown in the structures shown in FIG. 2 and Complexes 2 and 4 of FIG. 3. Additionally, the pendant phenyl groups may contain a different array of substituents in place of the fluoro substituents, for example, H, F, Cl, Br, —CN, optionally fluorinated $C_{1-3}$ alkyl, or optionally fluorinated $C_{1-3}$ alkoxy.

In other embodiments, Z in these compounds further or independently comprise at least one moiety capable of participating in a biorthogonal reaction, for example 1,3-dipolar cycloaddition reaction (including an alkene/alkyne and azide [3+2] cycloaddition), an alkene and tetrazine inverse-demand Diels-Alder reaction (e.g., comprising a three-membered and four-membered cycloalkene moiety, a reaction between nitrones and cyclooctynes, oxime/hydrazone formation from aldehydes and ketones, the isocyanide-based click reaction, and the quadricyclane ligation.

In still other embodiments, Z in these compounds further or independently are coordinated to at least one transition metal compound, which can act as a secondary catalyst, imaging agent, or therapeutic agent. Z may also conjugate (covalently or non-covalently) or be bonded to a drug, such as doxorubicin, paclitaxel, or docetaxel, or a fragment thereof or may be conjugated (covalently or non-covalently) or be bonded to a nanoparticle.

In still other embodiments Z in these compounds further or independently are conjugated (covalently or non-covalently) to a nucleic acid, protein, peptide, antibody (including monoclonal antibody), chimeric antigen receptor, transferrin, a ligand for a cellular receptor, or a cellular receptor protein, or alternatively a fragment of an antibody, transferrin, a ligand for a cellular receptor, a cellular receptor protein, or a cell-penetrating peptide. Z may also be conjugated (covalently or non-covalently) to a natural or synthetic carbohydrate, fat, fatty acid (e.g., oleic or linoleic acid), lipid, glyceride, or vitamin.

In certain specific embodiments, M is Al or Ga, preferably Ga, optionally coordinated to one or more axial ligands, typically pyridine.

Other aspects of the invention also include methods of making the inventive compositions, both the metallated and non-metallated corroles, in either single step or stage-wise syntheses.

Still other aspects of the invention also include pharmaceutical compositions comprising any of the inventive compounds in combination with one or more pharmaceutically acceptable inert ingredients and/or one or more therapeutic agents.

Still other aspects of the invention include methods of using these inventive compounds for the detection or treatment of a range of diseases or conditions, in the absence or presence of light. Such diseases or conditions can involve the inhibition of growth factor receptor tyrosine kinase activity. Other diseases or conditions can be cardiovascular disease or condition and/or cancer in a patient.

These embodiments are more fully described below.

BRIEF DESCRIPTION OF THE DRAWINGS

The present application is further understood when read in conjunction with the appended drawings. For the purpose of illustrating the subject matter, there are shown in the drawings exemplary embodiments of the subject matter; however, the presently disclosed subject matter is not limited to the specific methods of making and methods of using, processes, devices, and systems disclosed. In addition, the drawings are not necessarily drawn to scale. In the drawings:

FIG. 4B shows various modular corrole frameworks functionalized using 6-amino caproic acid for nucleophilic aromatic substitution at the para position of the fluorophenyl ring (Complex 1, left) and then subsequent coupling to free amines to form high-value functionalized corroles (right).

FIGS. 6A-D show cytotoxic effects of functionalized gallium(III) corroles on human cancer cells. Dose-response curves for a 72-h exposure of human tumor cell lines, prostate (DU-145), melanoma (SK-MEL-28), breast (MDA-MB-231), and ovarian (OVCAR-3) to (FIG. 6A) Complex 1, (FIG. 6B) Complex 2, (FIG. 6C) Complex 3, or (FIG. 6D) Complex 4 were evaluated using the MTS assay. The viability of each corrole-treated cell line is expressed as a percentage of untreated control growth. A sigmoidal dose-response curve was fitted to the data using GraphPad Prism 6. Data represent the mean±SD of three independent experiments.

DETAILED DESCRIPTION OF ILLUSTRATIVE EMBODIMENTS

Figure 1:
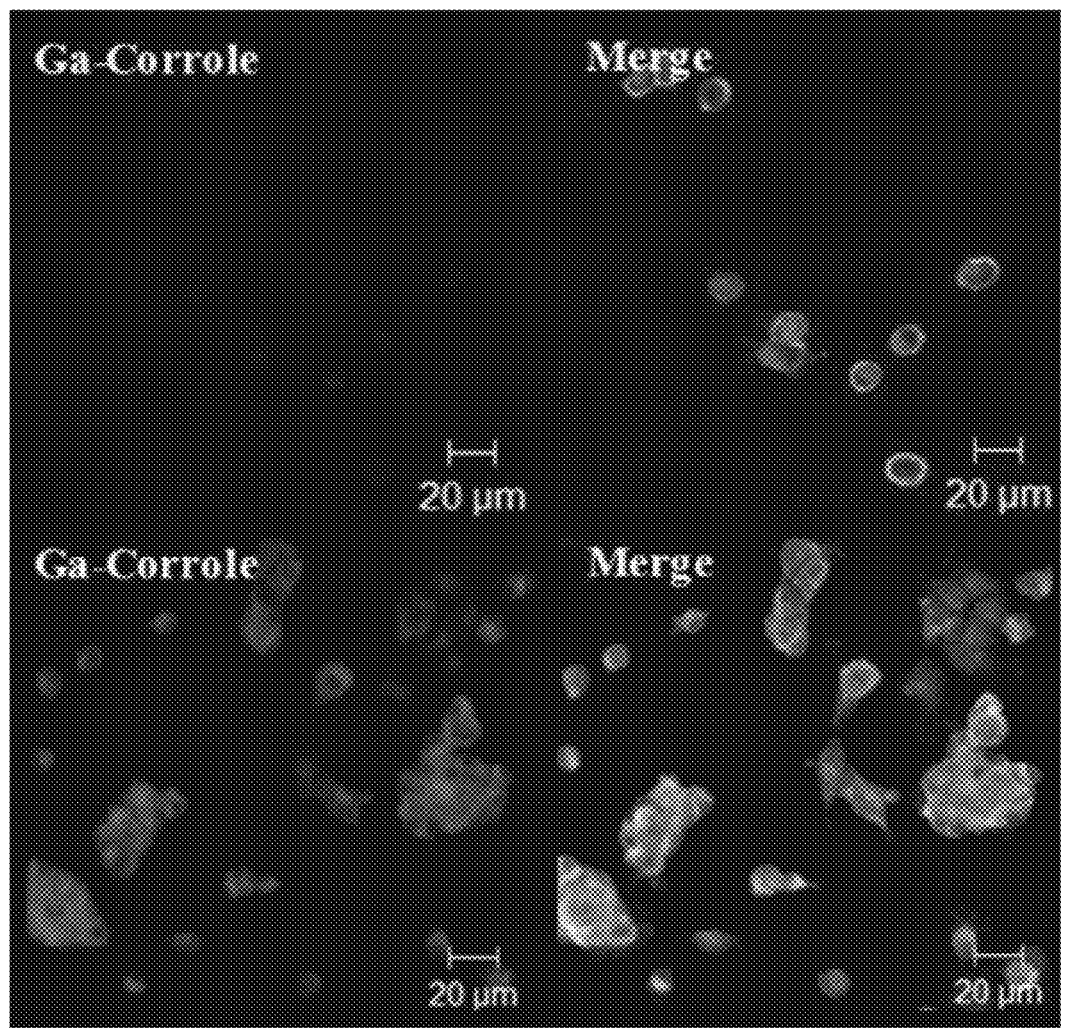
FIG. 1 shows intracellular accumulation of carboxylated corroles Complex 3 (top panels) and Complex 4 (bottom panels) in brain metastatic prostate carcinoma (DU-145). Cells on the left were incubated in a 3 µM solution of corrole for 3 h, then excited with 405 nm light. Red emission indicates the presence of corrole. Cells on the right were additionally stained with DAPI and WGA (labeled with AlexaFluor-488) to show the location of the nucleus in blue and the cell membrane in green, respectively.

The present invention is directed to derivatized corrole compounds, including metallocorroles, methods of making these derivatized corroles, and methods of using these derivatized corroles in the treatment of various diseases and conditions.

Corroles are macrocyclic molecules related to porphyrins and other aromatic macrocycles whose pharmacological properties have led to the development of many drugs. The synthesis of analogs, determination of pharmacokinetics, targeting, and bioavailability represent significant challenges to the realize the full potential of these drugs, since it is not always clear as to the effect of various functionalizations on the inherent therapeutic properties of these macrocyclic compounds.

Yet, corroles have received a great deal of attention in recent years. Of interest here is a gallium(III) complex 1 [Ga(tpfc)], where tpfc represents the trianion of 5,10,15-tris (pentafluorophenyl)corrole [$H_3$(tpfc)]. Complex 1 (see FIG. 3) is highly fluorescent, with an emission quantum yield far exceeding that of its zinc porphyrin analog. The macrocyclic ring of this complex can be selectively modified to afford molecules that exhibit a wide range of physical and chemical properties. Previous work focused on a sulfonic acid derivative of Ga(tpfc), Complex 2 [Ga(2,17-$S_2$tpfc)] (see FIG. 3); notably, Complex 2 possessed potent antitumor activity both in vitro (using human cancer cells) and in vivo (using murine model animals), making it a powerful reagent for both imaging and therapeutic targeting of cancer cells. Additional studies on the mechanism of cytotoxicity demonstrated that numerous cancer cell lines rapidly take up Complex 2 in vitro and induce cell cycle arrest at late M phase. Replacement of bis-sulfonic acids with para-pyridinium substituents (Complex 5, FIG. 3) was shown to improve uptake and activity, whereas ortho-pyridinium substitution (Complex 6, FIG. 3) completely ablated toxicity, indicating that functional group modifications of the corrole can have profound effects on biological activity.

Corroles, synthetic members of the tetrapyrrolic macrocycle family of porphyrins and corrins, are highly fluorescent and often exhibit cytotoxic and cytostatic behavior towards cancer cells. With optimized synthetic routes providing greater access to functionalized corroles and the increasing interest in macrocycles for cancer therapy, there is great potential for corroles to emerge as key players in the field of theranostics.

Importantly, the present invention describes a class of compounds that exhibit anticancer activity, in some cases this activity appears to be superior to cisplatin. This enhanced permeability is expected to enhance the activity of these compounds in other methods of treatment where corroles have been shown to be therapeutically effective. Further, these corroles exhibit this cytotoxicity in the presence or absence of photoexcitation. Installing aminocaproate on the fluorophenyl ring by nucleophilic aromatic substitution used mild conditions with biocompatible reagents, required only simple purification and provided ready access to other corroles. Carboxylated corroles are very rapidly taken up by cells, with an order of magnitude gain in dark cytotoxicity likely owing to greater cell permeability. With optimized synthetic routes providing greater access to functionalized corroles and the increasing interest in macrocycles for cancer therapy, there is great potential for corroles to emerge as cancer therapeutics and diagnostic imaging agents.

The observed selectivity for nuclear penetration in one type of prostate cancer is extremely promising for targeted drug delivery and for the development of macrocycle-based therapies. Since the identity of the functional group has such a dramatic effect on the biological activity of corroles, it is an enormous advantage that the tetrapyrrolic framework can be easily and systematically functionalized at different sites. With optimization, a functionalized corrole may be used as a diagnostic tool to identify the presence, extent, and precise location of prostate cancer tumors.

The present invention may be understood more readily by reference to the following description taken in connection with the accompanying Figures and Examples, all of which form a part of this disclosure. It is to be understood that this invention is not limited to the specific products, methods, processes, conditions or parameters described or shown herein, and that the terminology used herein is for the purpose of describing particular embodiments by way of example only and is not intended to be limiting of any claimed invention. Similarly, unless specifically otherwise stated, any description as to a possible mechanism or mode of action or reason for improvement is meant to be illustrative only, and the invention herein is not to be constrained by the correctness or incorrectness of any such suggested mechanism or mode of action or reason for improvement. Throughout this specification, claims, and drawings, it is recognized that the descriptions refer to compositions and processes of making and using said compositions. That is, where the disclosure describes or claims a feature or embodiment associated with a composition or a method of making or using a composition, it is appreciated that such a description or claim is intended to extend these features or embodiment to embodiments in each of these contexts (i.e., compositions, methods of making, and methods of using).

Terms

In the present disclosure the singular forms "a," "an," and "the" include the plural reference, and reference to a particular numerical value includes at least that particular value, unless the context clearly indicates otherwise. Thus, for example, a reference to "a material" is a reference to at least one of such materials and equivalents thereof known to those skilled in the art, and so forth.

When a value is expressed as an approximation by use of the descriptor "about," it will be understood that the particular value forms another embodiment. In general, use of the term "about" indicates approximations that can vary depending on the desired properties sought to be obtained by the disclosed subject matter and is to be interpreted in the specific context in which it is used, based on its function. The person skilled in the art will be able to interpret this as a matter of routine. In some cases, the number of significant figures used for a particular value may be one non-limiting method of determining the extent of the word "about." In other cases, the gradations used in a series of values may be used to determine the intended range available to the term "about" for each value. Where present, all ranges are inclusive and combinable. That is, references to values stated in ranges include every value within that range.

It is to be appreciated that certain features of the invention which are, for clarity, described herein in the context of separate embodiments, may also be provided in combination in a single embodiment. That is, unless obviously incompatible or specifically excluded, each individual embodiment is deemed to be combinable with any other embodiment(s) and such a combination is considered to be another embodiment. Conversely, various features of the invention that are, for brevity, described in the context of a single embodiment, may also be provided separately or in any sub-combination. Finally, while an embodiment may be described as part of a series of steps or part of a more general structure, each said step may also be considered an independent embodiment in itself, combinable with others.

The transitional terms "comprising," "consisting essentially of," and "consisting" are intended to connote their generally in accepted meanings in the patent vernacular; that is, (i) "comprising," which is synonymous with "including," "containing," or "characterized by," is inclusive or open-ended and does not exclude additional, unrecited elements or method or process steps; (ii) "consisting of" excludes any element, step, or ingredient not specified in the claim; and (iii) "consisting essentially of" limits the scope of a claim to the specified materials or steps "and those that do not materially affect the basic and novel characteristic(s)" of the claimed invention. Embodiments described in terms of the phrase "comprising" (or its equivalents), also provide, as embodiments, those which are independently described in terms of "consisting of" and "consisting essentially of." For those embodiments provided in terms of "consisting essentially of," particularly in the descriptions of methods of detection or therapy, the basic and novel characteristic(s) of a process is the ability of the compounds to exhibit such detection or therapy with or without added agents.

When a list is presented, unless stated otherwise, it is to be understood that each individual element of that list, and every combination of that list, is a separate embodiment. For example, a list of embodiments presented as "A, B, or C" is to be interpreted as including the embodiments, "A," "B," "C," "A or B," "A or C," "B or C," or "A, B, or C." Similarly, where a numerical range is presented, for example, "where m is independently 1-18," is to be appreciated as encompassing independent embodiments where m is, for example, 1, 2, 3, 4, etc. as well as ranges encompassing any sub-range within the genus range, for example, where m is in a range of from 1 to 2, from 2 to 3, from 1 to 6, from 12 to 18, etc. Likewise, a designation $C_{1-3}$ alkyl, for example, includes as independent embodiments $C_1$ alkyl $C_2$ alkyl, $C_3$ alkyl, $C_{1\ or\ 2}$ alkyl, $C_{2\ or\ 3}$ alkyl, $C_{1\ or\ 3}$ alkyl, as well as $C_{1,\ 2,\ or\ 3}$ alkyl.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, representative illustrative methods and materials are described herein.

Unless otherwise stated, ratios or percentages are intended to refer to mole percent or atom percent, as appropriate.

Throughout this specification, words are to be afforded their normal meaning, as would be understood by those skilled in the relevant art. However, so as to avoid misunderstanding, the meanings of certain terms will be specifically defined or clarified.

The term "administration" defined in terms of local or systemic delivery of the material to the patient, as described above. As used throughout this specification, reference to administering a compound also includes those embodiments where the compounds are administered as a pharmaceutical composition or in concert or sequentially with other therapeutic agents. The specific nature of the co-administered therapeutic agent depends on the nature of the disease or condition being treated or the additional effect required. Exemplary additional therapeutic agents include other anti-cancer agents (e.g., doxorubicin, paclitaxel, or docetaxel), thrombolytic agents, anti-emetic agents to treat nausea or emesis, anesthetics, agents useful in the treatment of anemia, an agent useful in the treatment of neutropenia, corticosteroids, non-steroidal anti-inflammatory drugs (NSAID), pain suppressants, analgesics, or the use of radiation therapy.

The term "conjugated," as in "Z may be conjugated to a nucleic acid" typically refers to attachment by covalent bonds, but may also refers to other non-covalent attachments by other means, e.g., hydrogen bonding.

The terms "method(s)" and "process(es)" are considered interchangeable within this disclosure.

"Optional" or "optionally" means that the subsequently described circumstance may or may not occur, so that the description includes embodiments where the circumstance occurs and instances where it does not. For example, the phrase "optionally coordinated to one or more ligands" means that a ligand may or may not be coordinated to the metal, M, and, thus, the description includes structures wherein a ligand or ligands are present and structures wherein a ligand is not present. Typically, these ligands are coordinated to M in an axial position relative to the plane of the corrole or porphyrin.

As used herein, the term "photodynamic therapy" ("PDT") refers to a method of treating malignancies, diseased tissue, hyperproliferating tissues, normal tissues or pathogens. PDT involves a localized or systemic administration of a photosensitizing compound followed by exposure of target tissue to photo-activating light. The photo-activating light excites the photosensitizer which, in turn, interacts with singlet oxygen causing the production of cytotoxic oxygen species. The interaction of the cytotoxic oxygen species with tissues in which the photosensitizer is localized causes a modification of the tissue, resulting in a desired clinical effect. For a more detailed description of photodynamic therapy, see U.S. Pat. Nos. 5,225,433; 5,198, 460; 5,171,749; 4,649,151; 5,399,583; 5,459,159; and 5,489,590. Each of these references is incorporated by reference herein at least for the methods, materials, and effects of photodynamic therapy.

The term "treating" or "treatment" as used herein comprises a treatment relieving, reducing or alleviating at least one symptom in a subject or effecting a delay of progression of a disease. For example, treatment can be the diminishment of one or several symptoms of a disorder or complete eradication of a disorder, such as cancer. Within the meaning of the present invention, the term "treat" also denotes to arrest, delay the onset (i.e., the period prior to clinical manifestation of a disease) and/or reduce the risk of developing or worsening a disease. Treatment may be done on patient exhibiting the disease or condition or prophylactically on a patient as risk of the disease or condition. The term "protect" is used herein to mean prevent delay or treat, or all, as appropriate, development or continuance or aggravation of a disease in a subject, e.g., a mammal or human.

The term "prevent," "preventing," or "prevention" as used herein comprises the prevention (e.g., the action of stopping something from happening or arising) of at least one symptom associated with or caused by the state, disease or disorder being prevented.

In the methods described herein, the amount of the administered compound represents a therapeutically effective amount of the compound, whether delivered in a single dosage form or multiple times over the course of a day. The term "therapeutically effective amount" is an amount sufficient to provide an observable improvement over the baseline clinically observable signs and symptoms of the disorder treated compound over the course of the treatment.

Compounds—Derivatized Corroles and Porphyrins

As described elsewhere herein, the present invention is directed, at least in part, to novel corrole and porphyrin compounds. Independent embodiments of the invention(s) include those where the compound(s) have a Formula (I-H), (I-M), (II-H), or (II-M):

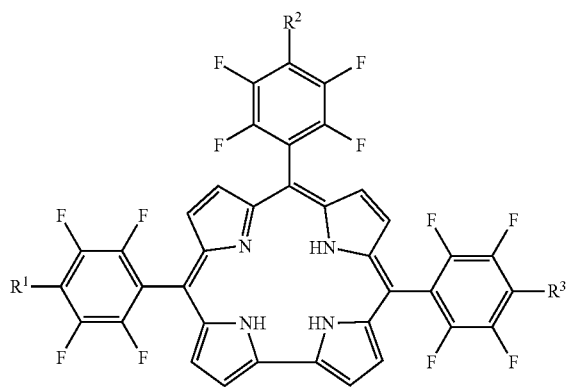
(I-H)

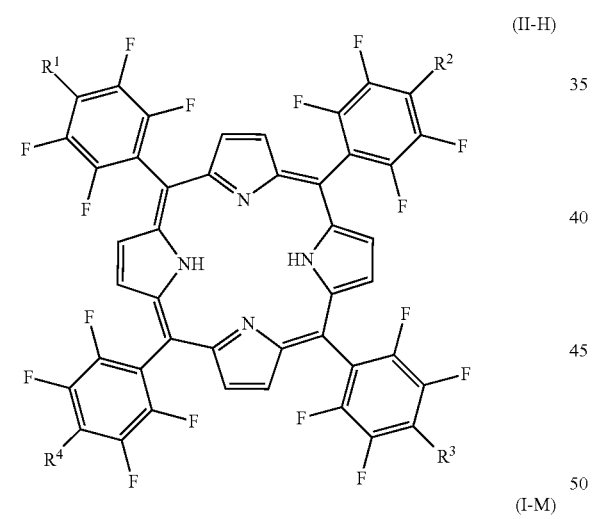
(II-H)

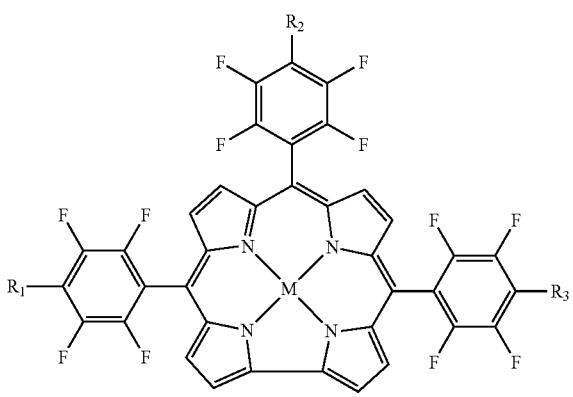
(I-M)

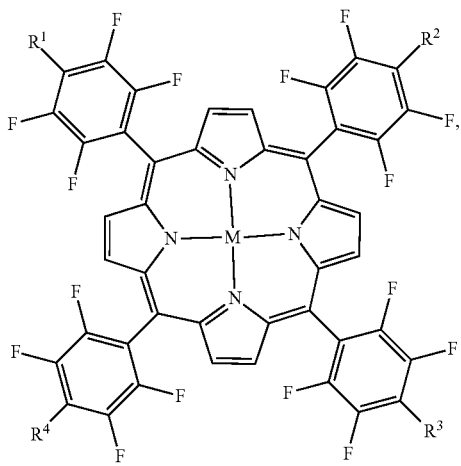
(II-M)

wherein
R$^1$, R$^2$, R$^3$, and R$^4$ are independently —F or —N(H)—(CH$_2$)$_m$—Y, provided that at least one of R$^1$, R$^2$, R$^3$, and R$^4$ is —N(H)—(CH$_2$)$_m$—Y;

—Y is —N(Z)$_2$, —O—Z, —C(O)—O—Z, —OC(O)Z—, —OC(O)O—Z, —C(O)N(Z)$_2$, —NH—C(O)—Z, —C(O)NHNH—Z

—Z is independently R$^5$, —(CH$_2$)$_m$—X, —(CH$_2$)$_m$—OR$^5$, —(CH$_2$)$_m$—SR$^5$, —(CH$_2$)$_m$—N(R$^5$)$_2$, —(CH$_2$CH$_2$O)$_n$—OR$^5$, —(CH$_2$CH$_2$O)$_n$—N(R$^5$)$_2$, —(CH$_2$)$_m$—N$_3$, —(CH$_2$)$_m$—C≡C—R$^5$, an amino acid, peptide, protein, polyol;

R$^5$ is independently H or C$_{1-12}$alkyl;

X is Cl, Br, or I;

m is independently 1-18 (preferably 1-12 or 1-6 or 1-2);

n is 1-32; and

M is Ag, Al, Co, Cr, Cu, Fe, Ga, Ge, Hf, Ir, Mo, Mn, Nb, Ni, Os, Pt, Re, Rh, Ru, Sb, Sn, Ta, Ti, V, or W, a lanthanide or actinide, or an isotope or radionuclide thereof, each of which is optionally coordinated to one or more ligands.

Figure 2:
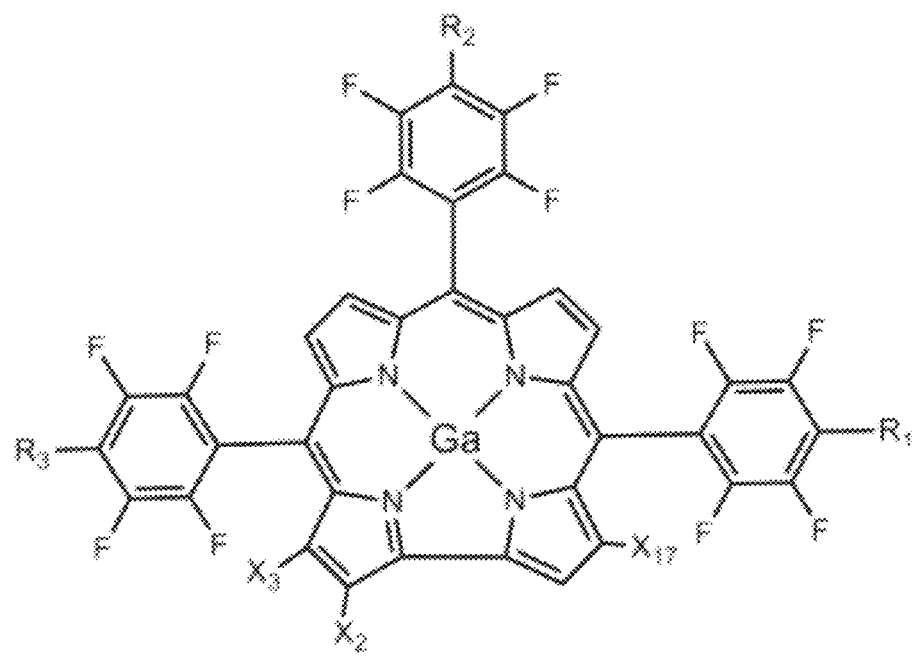
FIG. 2 shows modular corrole frameworks functionalized with aminocaproic acid at the para position (R1) of the 5-fluorophenyl ring (Complex 3), carboxylate at the β-pyrrolic X3 position (Complex 4) and sulfonate at β-pyrrolic X17 and X2 sites (Complex 2).
Figure 3:
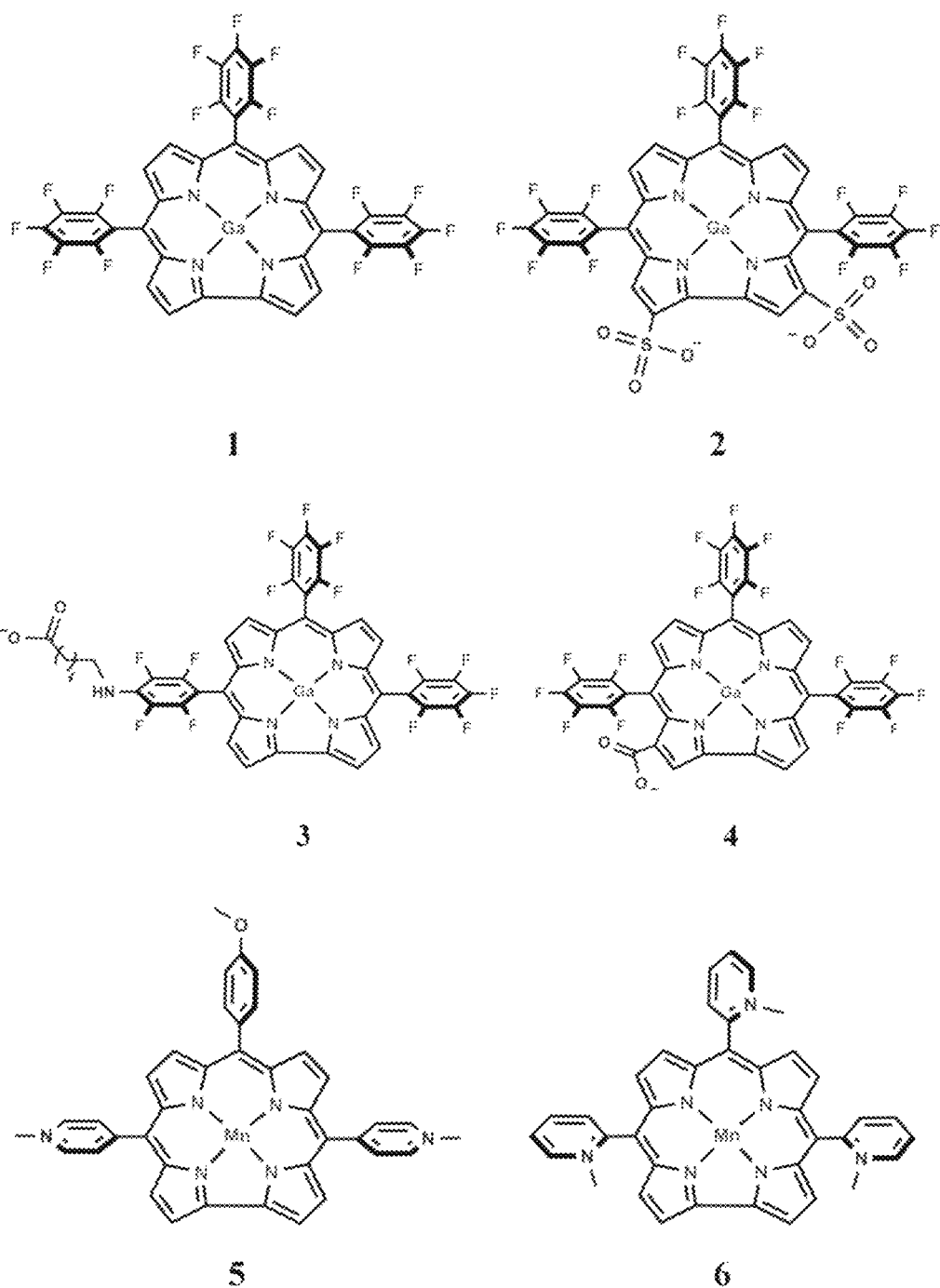
FIG. 3 shows structures of functional group-substituted derivatives of corroles. For clarity, the axial pyridine is not shown in the structures.

In some embodiments, one or more of the macrocyclic ring pyrroles may each be substituted with one or two carboxylic acid (or carboxylate) or sulfonic acid (or sulfonate) moieties, X$^1$, e.g., where the macrocyclic rings systems are as shown in Structures (I-H"), (II-H"), (I-M"), or (II-M"), or, for example, as shown in the structures shown in FIG. 2 and Complexes 2 and 4 of FIG. 3. Such substitutions are described in U.S. patent application Ser. No. 14/178,592, which is incorporated by reference at least for its teachings of the substitution patterns available for the macrocyclic ring pyrroles and phenyl rings, the methods of providing such substitutions, and for methods of attaching such substituted materials to nanoparticles.

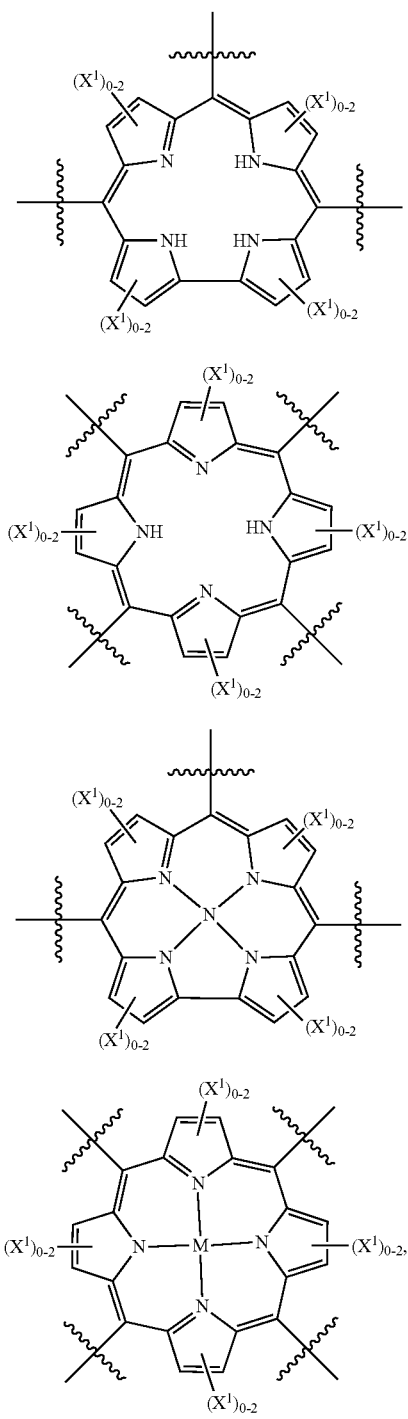

(I-H″)

(II-H″)

(I-M″)

(II-M″)

Additionally, while compounds comprising the fluorinated phenyl groups are commonly used in the art, the pendant phenyl groups are not necessarily limited to this substitution pattern. Separate embodiments provide that the phenyl groups contain a different array of substituents in place of the fluoro substituents, for example according to Formula (III), where $X^2$ is independently H, F, Cl, Br, —CN, optionally fluorinated $C_{1-3}$ alkyl, or optionally fluorinated $C_{1-3}$ alkoxy and $R^5$ is $X^2$ or —N(H)—$(CH_2)_m$—Y, as described elsewhere herein:

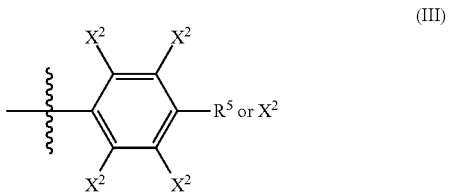

(III)

Any reference made herein to any of the compounds described as having a Formula (I), (I-H), (I-M), (II), (II-H), or (II-M) also includes, as separate embodiments, compounds in which the macrocyclic ring pyrroles and/or the pendant phenyl rings are optionally substituted as described above. The specific use of the para substitutent $X^2$ or $R^5$ depends on the context in which the substituents are described. For example, separate embodiments include those where the compound described in terms of Formula (I) or Formula (II) (or a corresponding structure comprising substituted macrocyclic pyrrole(s)), are substituted according to the structure of Formula (III) where the para substituent in the structure of Formula (III) is as provided for $X^2$ (i.e., independently H, F, Cl, Br, —CN, optionally fluorinated $C_{1-3}$ alkyl, or optionally fluorinated $C_{1-3}$ alkoxy). In the case where the compound is described in terms of Formulas (I-H), (I-H″), (II-H), (II-H″), (I-M), (I-M″), (II-M), or (II-M″), independent embodiments also include those where the para substituent in the structure of Formula (III) is $R^5$ (i.e., where $R^5$ is $X^2$ or —N(H)—$(CH_2)_m$—Y).

Each permutation within these descriptions as considered an independent embodiment. Also note that both corroles and porphyrins are highly conjugated systems, wherein a number of resonance structures are available. The depictions herein provide but one of the many equivalent ring structures for these compounds.

As described above, $R^1$, $R^2$, $R^3$, and $R^4$ are independently —F or —N(H)—$(CH_2)_m$—Y, provided that at least one of $R^1$, $R^2$, $R^3$, and $R^4$ is —N(H)—$(CH_2)_m$—Y. That is, in separate embodiments, one, two, or all three of $R^1$, $R^2$, and $R^3$ in the compounds of Formulas (I-H) and (I-M) and one, two, three, or all four of $R^1$, $R^2$, $R^3$, and $R^4$ in the compounds of Formulae (II-H) and (II-M) are independently functionalized according to —N(H)—$(CH_2)_m$—Y. In the corroles, at least, mono-substitution appears to favor, though not necessarily exclusively, substitution of the phenyl group in the 5-position.

In certain embodiments, Z is or comprises an amino acid, peptide, protein, polyol, or polyglycol, such as polyethyleneglycol. Such appendages provide useful means for attaching to larger biological moieties, chelating certain transition or other metals, or imparting solubility or targeting properties. In its most general sense, the term amino acid includes any compound containing both an amine group and a carboxylic acid group (or protected versions thereof). In specific embodiments, the term also refers to naturally occurring amino acids (and their achiral or racemic derivatives), for example arginine, lysine, aspartic acid, glutamic acid, glutamine, asparagine, histidine, serine, threonine, tyrosine, cysteine, methionine, tryptophan, alanine, isoleucine, leucine, phenylalanine, valine, proline, and glycine. As seen in the Examples, arginine is an attractive amino acid for this purpose. The term "peptide" confers is normal meaning, i.e., a compound consisting of two or more amino acids linked in a chain, the carboxyl group of each acid being joined to the amino group of the next by a bond of the type —OC—NH—. Amino acids that have been incorporated into peptides are termed "residues" due to the release of either a hydrogen ion from the amine end or a hydroxyl ion from the carboxyl end, or both, as a water molecule is released during formation of each amide bond. The term encompasses dipeptides, tripeptides, tetrapeptides, etc., including also polypeptide. Peptides fall under the broad chemical classes of biological oligomers and polymers, alongside nucleic acids, oligosaccharides and polysaccharides, etc. the terms peptides and proteins are generally distinguished by the number of linked amino acids.

Exemplary polyols (i.e., an alcohol containing multiple hydroxyl groups) include natural and artificial sweeteners, for example, saccharides (e.g., glucose and sucrose) and polysaccharides, sorbitol, xylitol, mannitol and maltitol.

In addition to the specific substituents described for Z, it should be appreciated that the functional groups of Z may further be conjugated with other species.

For example, in some embodiments, Z is further modified to comprise a moiety or moieties (e.g., alkyne, azide, alkene or strained alkene) capable of participating in a biorthogonal reaction, for example 1,3-dipolar cycloaddition reaction (including an alkyne/alkene and azide [3+2] cycloaddition, sometimes referred to as a Huisgen Azide-Alkyne 1,3-Dipolar Cycloaddition), strain-promoted alkyne-nitrone cycloaddition, or an alkene and tetrazine inverse-demand Diels-Alder reaction (e.g., comprising a three-membered and four-membered cycloalkene moiety), oxime/hydrazone formation from aldehydes and ketones, a isocyanide-based click reaction, or a quadricyclane ligation. As described in the Examples, Z may be functionalized to participate in so-called "click" chemistry, and specific embodiments. It should also be appreciated that the reaction of any such "click-derivatized" compound with a complementary reagent in this type of chemistry is also considered within the scope of the present invention.

In other embodiments, Z is further modified to chelate or be coordinated to a transition metal compound, for example Pt. Z may also conjugate or be bonded to a drug, such as doxorubicin, paclitaxel, or docetaxel, or a fragment thereof. Similarly, Z may be conjugated or be bonded to a nanoparticle, such as carbon nanoparticles (e.g., carbon nanotubes or fullerenes), semiconductor or quantum dots, or nano-particulate oxides (for example, comprising $SiO_2$, $TiO_2$, or $ZrO_2$)

In other embodiments, Z is, comprises, or is conjugated to at least one biomolecule, for example, nucleic acid, protein, antibody (including monoclonal antibody), chimeric antigen receptor, transferrin, a ligand for a cellular receptor, or a cellular receptor protein, or alternatively a fragment of an antibody, transferrin, a ligand for a cellular receptor, a cellular receptor protein, or a cell-penetrating peptide. In still other embodiments, Z comprises, or is conjugated to at least one natural or synthetic carbohydrate, fat, fatty acid (e.g., oleic or linoleic acid), lipid, glyceride, or vitamin (e.g., folic acid). In other embodiments, Z comprises or is conjugated to glucosamine and/or cell-penetrating peptides.

Such structures may possess both imaging and anti-cancer therapeutic activity. These tools, which may be referred to as antibody-corrole-drug conjugates (ACDCs) or antibody-porphyrin-drug conjugates (APDCs), are based on the marriage of multiple well-studied anti-cancer technologies. Functionalized gallium corroles, for example, have been shown to aid in both fluorescence detection and dark elimination of cancer cells in murine models, and can act as multi-therapeutic imaging and cytotoxic reagents. Gallium corroles, in particular, can be easily attached to tumor-targeting antibodies, known anti-cancer drugs or a combination of the two; these auxiliary moieties can play a role in targeting of the constructs to cancer cells and could enhance the activity of the drugs. Using the proposed ACDC or APDC reagents, which are discrete, covalently-bound constructs, it may be possible to target and eradicate tumors while monitoring the progress of therapy with standard imaging techniques. In this way, ACDCs or APDCs will be truly multi-therapeutic.

The identity of the metal center is important for the biological activity of these tetrapyrrolic macrocycles, particularly corroles. Of the metals listed herein, Al, Ga, Co, and Mn are of particular interest. Cobalt is of interest since exposure of an alkylcobalamin using 660 nm light leads to photo-triggered dissociation of axially-coordinated drugs, offering a potential drug delivery mechanism.

As used herein, and as would be understood by those skilled in the art, the term "lanthanide or actinide" refers to those f-block elements, including the fifteen metallic chemical elements with atomic numbers 57 through 71, from lanthanum through lutetium as well as the 15 elements with atomic numbers from 89 to 103, actinium through lawrencium. The fifteen lanthanide elements, along with the chemically similar elements scandium and yttrium, are often collectively known as the rare earth elements.

With respect to the central metal, M, in the compounds of Formula (I-M) and (II-M), M is defined in terms of a range of elements, along with their respective isotopes or radionuclides. In each case, it is to be understood that M exists in an oxidation state appropriate for its position in the macrocyclic corrole or porphyrin, as would be understood by this of skill in the art. Further, reference to any given metal, M, is to be understood to refer to the metal in its naturally occurring state (with respect to isotopic distribution) as well as optionally including elements in enriched isotopic states, for example, for use as radionuclides for use as radio-imaging labels. In the particular case of gallium, reference to Ga is intended to connote Ga in its natural oxidation state, as well as Ga optionally independently enriched in Ga-67 and Ga-68. Gallium-67 decays by gamma emission with a half-life of 3.3 days, and is a well-studied contrast agent for radiography and computed tomography (CT) imaging techniques, in particular single photon emission computed tomography (SPECT). Gallium-68, with a half-life of 68 minutes, decays by positron emission and is therefore an appropriate reagent for positron emission tomography (PET) imaging. It can be extracted with relative ease from a portable generator containing germanium-68, which has a half-life of 271 days. The associated antibody-corrole-drug conjugate (ACDC) or antibody-porphyrin-drug conjugate (APDC) reagents for use as selective tumor cell targeting and eradication can be radiolabeled with a simple change in the order of reaction sequence Also with respect to the central metal, M, in the compounds of Formula (I-M) and (II-M), each M is optionally coordinated to one or more axial ligand. The specific nature of each ligand depends on the nature of the metal, M, and the synthetic conditions to which the metallocorrole is exposed. These ligands may be neutral or more electronegative than the M to which they are coordinated. Neutral ligands include amines, nitriles, phosphines, sulfonated phosphines, phosphites, phosphinites, phosphonites, arsines, stibines, ethers, amines, amides, imines, sulfoxide, a heterocycle containing nitrogen, sulfur, oxygen, or a mixture thereof (for example, pyridine), thioethers, but tend to be nitrogen or phosphorus donor ligands, again depending on the natures of the metal. In some cases, depending on the oxidation state of M, the ligands may be more electronegative to the extent of being considered anionic ligands so as necessary to balance charge, anionic ligands, and may comprise, for example carboxylates (preferably acetate) or halides (preferably Br, Cl, or I).

U.S. Patent Application Publ. No. 2010/0305335 provides methods of incorporating transition metals (at least including Co, Ir, Os, Pt, Rh, and W) into corrole frameworks. U.S. Pat. No. 6,462,192 provides methods of incorporating transition metals (at least including Sn) into corrole frameworks. U.S. Pat. No. 6,939,963 provides methods of incorporating transition metals (at least including Al, Cr, Fe, Mn, Rh, Ru, and Sn) into corrole frameworks. U.S. Pat. No. 8,791,099 provides methods of incorporating transition metals (at least including Co, Cr, Cu, Fe, Mn, Rh, Ru, and V) into corrole frameworks. Each of these references is incorporated by reference herein for all purposes, but with respect to their teachings of the methods of making and characterizing metallocorrole and metalloporphyrin complexes, and their uses.

In certain specific embodiments of the present inventions, M is Al, Cr, Co, Fe, Ga, Mn, Rh, Ru, or Sn having 0, 1, or 2 axial nitrogen donor ligands. Such nitrogen donor ligands include tertiary or aromatic amine ligands, for example, at least trialkyl amines, pyrazine, pyridine, pyrimidine, quinoline, isoquinoline. Based on common industry practice for such corroles and porphyrins, pyridine or trimethyl amine appears to be preferred.

In other embodiments, M is Co, Cr, Fe, Ga, Ir, Mn, Rh, Ru, or Sn having 0, 1, or 2 axial phosphine ligands. Again, based on common industry practice for such corroles and porphyrins, triphenylphosphine ligands appear to be preferred.

In specific embodiments, M is Al or Ga, optionally coordinated to one or more ligands. Within these embodiments, M is Ga(III) having 0, 1, or 2 axial tertiary or aromatic amine ligands, preferably axial pyridine ligands, more preferably having one axial pyridine ligands.

Methods of Making the Compounds

The rich chemistries associated with the inventive compounds derives from the methods of their making. In general, the methods depend from the nucleophilic substitution by amine nucleophiles onto pendant pentafluorophenyl substituents of the precursor corroles or porphyrins, and the ability to further functionalize the first and second formed derivatives. For example, certain embodiments comprise synthetic methods, each method comprising contacting a compound of Formula (I) or Formula (II)

(I)

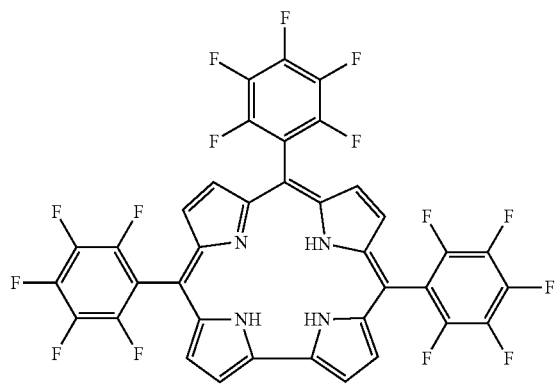

(II)

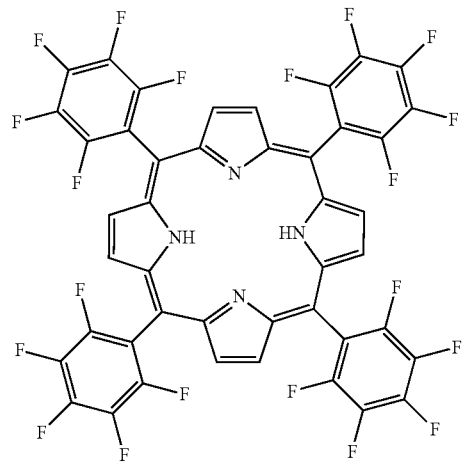

with a nitrogen nucleophile in the presence of base under conditions to form a compound of Formula (I-H) or (II-H), respectively, so as to form the compound of Formula (I-H) or (II-H), (I-H)

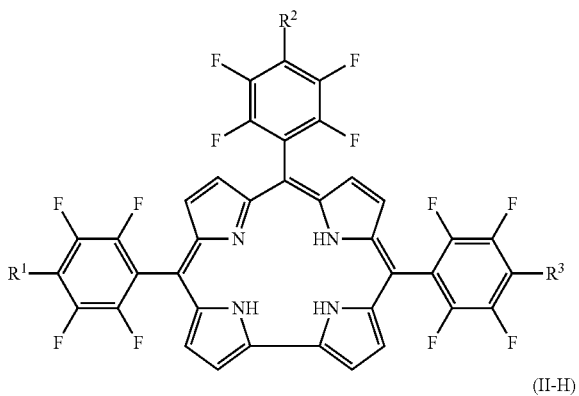

(II-H)

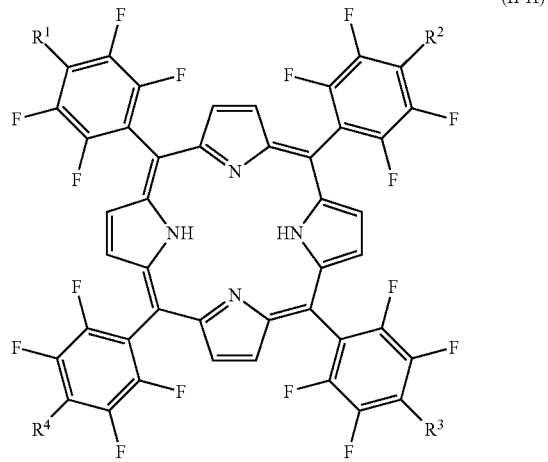

wherein the nitrogen nucleophile is $H_2N-(CH_2)_m-Y$, wherein $R^1$, $R^2$, $R^3$, and $R^4$ are independently —F or —N(H)—$(CH_2)_m$—Y, provided that at least one of $R^1$, $R^2$, $R^3$, and $R^4$ is —N(H)—$(CH_2)_m$—Y;

—Y is —N(Z)$_2$, —O—Z, —C(O)—O—Z, —OC(O)Z—, —OC(O)O—Z, —C(O)N(Z)$_2$, —NH—C(O)—Z, —C(O)NHNH—Z

—Z is independently R$^5$, —(CH$_2$)$_m$—X, —(CH$_2$)$_m$—OR$^5$, —(CH$_2$)$_m$—SR$^5$, —(CH$_2$)$_m$—N(R$^5$)$_2$, —(CH$_2$CH$_2$O)$_n$—OR$^5$, —(CH$_2$CH$_2$O)$_n$—N(R$^5$)$_2$, —(CH$_2$)$_m$—N$_3$, —(CH$_2$)$_m$—C≡C—R$^5$, an amino acid, peptide, protein, polyol;

R$^5$ is independently H or C$_{1-12}$alkyl;

X is Cl, Br, or I;

m is independently 1-18 (preferably 1-12 or 1-6 or 1-2) and n is 1-32.

Again, as described elsewhere herein, macrocyclic ring pyrroles may also be substituted with one or more carboxylic acid (or carboxylate) or sulfonic acid (or sulfonate) moieties. Additionally or alternatively, the pendant phenyl groups of Formulas (I-H), (I-H"), (II-H), or (II-H") may contain a different array of substituents in place of the fluoro substituents, as described elsewhere for Formula (III) for such structures.

Typical bases employed in these reactions include alkali metal (e.g., Li$^+$, Na$^+$, K$^+$, Rb$^+$, or Cs$^+$) or alkaline earth metal (e.g., Mg$^{2+}$, Ca$^{2+}$, Sr$^{2+}$, or Ba$^{2+}$), hydroxides, carbonates, or bicarbonates, or amines. Reaction media for such reactions may comprise polar protic or aprotic solvents, such as C$_{1-5}$ alcohols, ketones (e.g., acetone), alkyl acetates (e.g., ethyl acetate), dichloromethane, dimethylsulfoxide (DMSO), dimethylformamide, dimethylacetamide, dioxanes, N-methylformamide, propylene carbonate, pyridine, tetrahydrofuran, 2-methyl tetrahydrofuran, or mixtures thereof. Exemplary conditions are described in the Examples for the formation of Complex 3.

Additional embodiments include those where the initial nitrogen nucleophile is H$_2$N—(CH$_2$)$_m$—Y, wherein Y is —NH$_2$, —OH, or —C(O)OH, and the resulting product is optionally further functionalized with appropriate reagents to arrive at the compositions otherwise described herein (i.e., including amino acids, peptides, proteins, polyols, polysaccharides, click chemistry moieties, nucleic acids, antibodies, transferrin, ligands for a cellular receptor, or cellular receptor proteins, or fragments of antibodies, transferrin, ligand for cellular receptors, or cellular receptor proteins, carbohydrates, fats, lipids, glycerides, or vitamins). For example, the methods may further comprise reacting the resulting products with a reagent, wherein:

(a) when Y is —NH$_2$, the reagent is Z—X or Z—C(O)OH, (b) when Y is —OH, the reagent is Z—X, Z—C(O)OH, or Z—OC(O)OH, or (c) when Y is —C(O)OH, the reagent is Z—X, HN(Z)$_2$, or H$_2$NNH—Z, under conditions to form a compound of Formula (I-H) or (II-H) (where Y is —NH$_2$, —OH, or —C(O)OH, respectively), so as to form the compound of Formula (I-H) or (II-H) (comprising the more expanded definitions of Y).

The nucleophilic substitution may be performed on the metallated or non-metallated macromolecules. Where the metallated macrocycles are derivatized, the resulting product may contain a metal M having a pre-specified ligand, resulting from the presence of an associable ligand in the reaction medium, either as a (co)solvent (e.g., pyridine) or added material (e.g., PPh$_3$).

Metals may be incorporated into the derivatized or non-derivatized macromolecules using methods known to work on analogues of the inventive materials. In certain embodiments, the methods comprise reacting the compounds of Formula (I), (I-H), (II), or (II-H) with a precursor compound or salt of Al, Co, Cr, Cu, Fe, Ga, Ge, Ir, Mo, Mn, Os, Pt, Re, Rh, Ru, Sb, Sn, Ti, V, or W, under conditions to produce the metallated derivative. In the case where the starting material is a compound of Formula (I-H) or (II-H) a compound of Formula (I-M) or (II-M), so as to produce the compound of Formula (I-M) or (II-M)

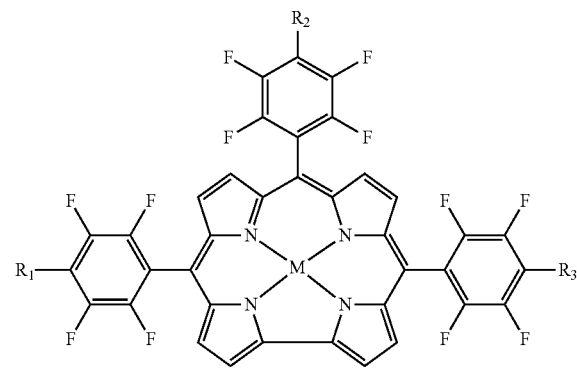

(I-M)

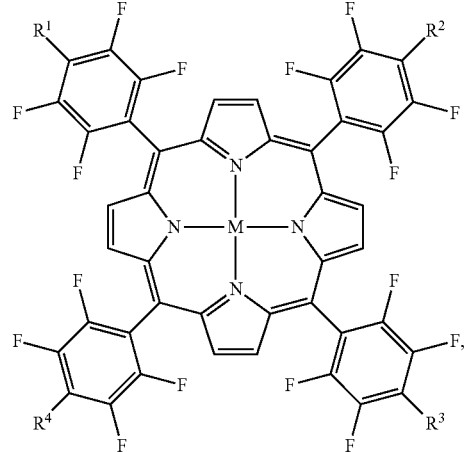

(II-M)

wherein M is Ag, Al, Co, Cr, Cu, Fe, Ga, Ge, Hf, Ir, Mo, Mn, Nb, Ni, Os, Pt, Re, Rh, Ru, Sb, Sn, Ta, Ti, V, or W, a lanthanide or actinide, or an isotope or radionuclide thereof, each of which is optionally coordinated to one or more axial ligands, as described elsewhere. Again, the macrocyclic ring structures and pendant phenyl groups may also be optionally or alternatively substituted as described elsewhere.

Pharmaceutical Compositions

As described herein, the inventive compounds are useful for a range of detection and therapeutic applications. In such cases, the compounds may be incorporated into formulations suitable for mammalian, including human, consumption. Certain embodiments include those pharmaceutical compositions comprising a pharmaceutically acceptable inert ingredient and any of the inventive compounds described herein, including metallated or non-metallated corroles or porphyrins. Such pharmaceutical compositions may further comprise a second or additional pharmaceutically active ingredient, dependent on the disease or condition being detected or treated. Likewise, those methods of detection or treatment described elsewhere herein may also comprise the administration of additional therapeutic agents, either with or separate from the administration of the inventive compounds.

As used herein the term "pharmaceutically acceptable inert ingredient" to be specified as a carrier, diluent, or excipient, such as are described in Remington: The Science and Practice of Pharmacy, Nineteenth Ed (Easton, Pa., Mack Publishing Company, 1995); Hoover, John E., Remington's Pharmaceutical Sciences, Mack Publishing Co., Easton, Pa. 1975; Liberman, H. A. and Lachman, L., Eds., Pharmaceutical Dosage Forms, Marcel Decker, New York, N.Y., 1980; and Pharmaceutical Dosage Forms and Drug Delivery Systems, Seventh Ed. (Lippincott Williams & Wilkins 1999), herein incorporated by reference for such disclosure.

The pharmaceutical compositions may be formulated in unit dosage forms suitable for local or systemic administration. Formulations for local administration may comprise means suitable for perivascular delivery, pericardial delivery into perivascular sac, periadventital delivery, intravascular delivery using elution from placed stents impregnated with corrole or porphyrin, endovascular delivery using balloon catheters with micropores or channels, or transmural injection ports pressurized and enhanced by mechanical and electrical means to facilitate intramural and transmural penetration of the corrole or porphyrin into the target tissue. Formulations for systemic administration include formulations suitable for oral, inhalation, or parenteral (e.g., intravenous, intravascular, intradermal subcutaneous, intramuscular) administration, for example in the form of a dispersion, solution, suspension, tablet, capsule, or pill. Methods of preparing such formulations are known in the art.

In some embodiments, the compound are formulated by encapsulation in carriers selected from water, deionized water, phosphate buffered saline, aqueous ethanol, glucose, amino acids, vegetable oils, liposomes, immunoliposomes, cyclodextrans, microspheres, nanoparticles, lipoproteins, micellular systems or combinations thereof. In other embodiments, the compounds are formulated as a slow release formulation (including compositions in which the compounds are incorporated into polymer or gel matrices), tablets, pills, solutions, suspensions, emulsions, granules or capsules.

Such formulations are described, for example, in U.S. Pat. No. 6,730,666, which describes the pharmaceutical composition of corroles in terms of oral administration or injection, e.g. intravenously or subcutaneously, or by conjugation to locally implanted stents. U.S. Pat. No. 8,791,099 describes the pharmaceutical composition of corroles in terms of oral and parenteral administration. The doses are said to depend on the type of disease or disorder and condition and age of the patient and may vary between 0.1 to 10 mg/kg/day. Each of these references is incorporated by reference in their entirety, or at least for their teachings of formulation and administration, and for their teachings of the compounds and methods of treating patients therewith.

In specific embodiments, the pharmaceutical comprise compounds having a Formula (I-M), where M is Al or Ga, optionally coordinated to one or more ligands. In certain aspects of these embodiments, M is Ga(III) having 0, 1, or 2 axial tertiary or aromatic amine ligands, preferably one axial pyridine ligand.

Methods of Use—Detection and Treatment of Diseases or Conditions

The use of corroles as therapeutic and imaging agents are known in the art, as are those uses related to porphryins. The compounds of the present invention provide significant improvements to the existing materials, yet they can be expected to act as these agents, as evidenced by the results described in the Examples. In certain embodiments, and as evidenced herein, corroles, once administered to a patient act in absence of light or with the application of light of a suitable wavelength and intensity (e.g., by so-called photodynamic therapy). The porphyrins appear to perform better with the application of the light.

For example, U.S. Pat. No. 6,730,666 describes the use of metallated macrocyclic molecules, such as corroles and porphyrins, as inhibitors of growth factor receptor tyrosine kinase activity, which activity is implicated in a range of diseases or conditions, including angiogenesis, atherosclerosis, hyperthrophic heart failure, postsurgical restenosis, primary tumors and metastasis, nonmalignant tumors, diabetic retinopathy, psoriasis, rheumatoid arthritis, retrolental fibroplasia, macular degeneration, hemangioma, arteriovenous malformation, hypertrophic scars, acne, scleroderma and autoimmune diseases, or bone and cartilage related disorders and inherited skeletal disorders selected from the group consisting of achondroplasia, dwarfism and craniosynostosis. U.S. Pat. No. 6,730,666, is incorporated by reference in its entirety, or at least for its teaching of this effect, the methods of treatment, the conditions treated, and the methods of preparing the metallated macrocyclic molecules, described therein.

Certain embodiments of the present invention, then, include those methods of inhibiting growth factor receptor tyrosine kinase activity, the method comprising administering to a patient in need of such treatment any of the compounds described herein.

In some of these embodiments, the growth factor receptor tyrosine kinase is selected from the group consisting of fibroblast growth factor (FGF) receptor tyrosine kinase, epidermal growth factor (EGF) receptor tyrosine kinase, heparin-binding EGF-like growth factor (HB-EGF) receptor tyrosine kinase, platelet derived growth factor (PDGF) receptor tyrosine kinase, vascular endothelial growth factor (VEGF) receptor tyrosine kinase, nerve growth factor (VGF) receptor tyrosine kinase, hepatocyte growth factor (HGF) receptor tyrosine kinase, insulin receptor tyrosine kinase and insulin-like growth factor (IGF) receptor tyrosine kinase. In these methods, the administration of the compounds of the present invention (i) inhibits angiogenesis; (ii) inhibits vascular smooth muscle cell proliferation in disorders selected from the group consisting of atherosclerosis, hyperthrophic heart failure and postsurgical restenosis; (iii) inhibits cell proliferation and migration in the treatment of primary tumors and metastasis; (iv) treats nonmalignant tumors; (v) treats diabetic retinopathy, psoriasis, rheumatoid arthritis, retrolental fibroplasia, macular degeneration, hemangioma, arteriovenous malformation, hypertrophic scars, acne, scleroderma and autoimmune diseases; or (vi) treats bone and cartilage related disorders and inherited skeletal disorders selected from the group consisting of achondroplasia, dwarfism and craniosynostosis.

In another field of use, U.S. Pat. No. 8,791,099 describes the use of metallocorroles in the detection and treatment of cardiovascular disease or conditions, wherein the cardiovascular disease or disorder comprises atherosclerosis, congestive heart failure, myocardial infarction, myocardial ischemia, or reperfusion. Again, as the present compounds represent improvements on this compounds discussed in this patent, and may be expected to otherwise operate in a similar fashion, independent embodiments of the present invention comprise administering any of the compounds described herein to a patient in need of such treatment; i.e., including any disease or condition described in U.S. Pat. No. 8,791,099, which is incorporated by reference at least for its teaching of this effect, the methods of treatment, the conditions treated, and the methods of preparing the metallocorroles described therein. That is, embodiments of the present invention include administering any of the compounds described herein to a patient in need of treating atherosclerosis, congestive heart failure, myocardial infarction, myocardial ischemia, or reperfusion.

Again, these methods include the use of compounds of Formula (I-M) or (II-M)

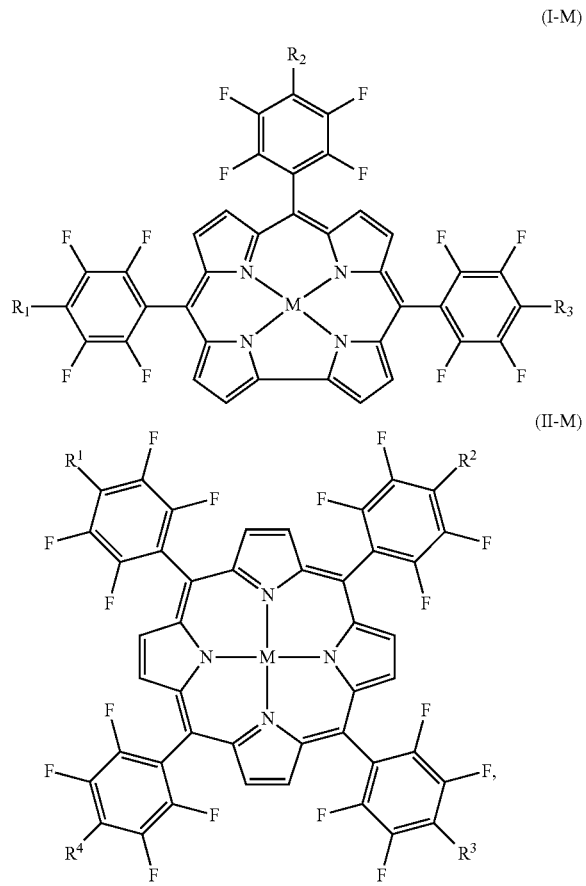

or optionally substituted versions thereof (i.e., where the macrocyclic pyrroles and pendant phenyl groups are optionally or alternatively substituted as described elsewhere). Particularly useful compounds include those where M is Al, Co, Fe, Ga, or Mn, optionally coordinated to one or more ligands, as discussed elsewhere herein.

As shown in the Examples, the compounds of the present invention provide significant advantages over other corrole materials in treating cancer, in some cases outperforming the well-known cisplatin in this capacity. Accordingly, still other embodiments of the present invention, include methods of detecting or treating cancer in a patient, each method comprising administering to a patient known or suspected of being afflicted by cancer any of the compounds described herein. As used herein, the term "cancer" refers to an abnormal growth of cells which tend to proliferate in an uncontrolled way and, in some cases, metastasizes. As exemplified in the Examples, cancer being treated may include leukemia, lung cancer, colon cancer, CNS cancer, melanoma, ovarian cancer, renal cancer, prostate cancer, or breast cancer. In particular embodiments, the compound is a compound of Formula (I-M). Note again here, that the present work shows the ability of corroles and metallated corroles to be cytotoxic in the absence of incident irradiation. Preferred compounds include those compounds of Formula (I-M), where M is Al or Ga, optionally coordinated to one or more ligands, more preferably where M is Ga(III) having 0, 1, or 2 axial tertiary or aromatic amine ligands, and even more preferably where the axial ligand is pyridine ligands, preferably one axial pyridine ligand.

Figure 4A:
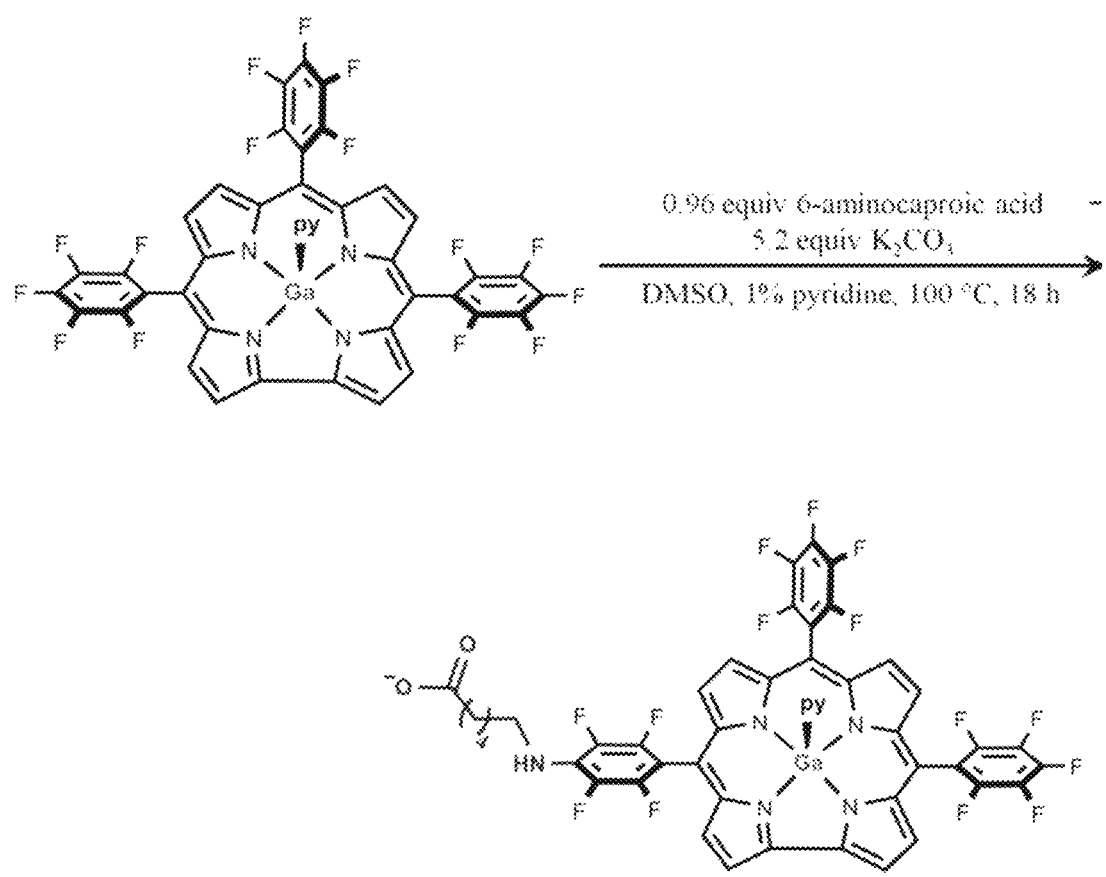
FIG. 4A shows a synthetic scheme for Complex 3 [Ga (ACtpfc)]. Reagents and conditions: 6-aminocaproic acid, $K_2CO_3$, DMSO, 1% pyridine, 100° C., 18 h.

Since an existing imaging technique uses the inherent upregulation of choline kinase in cancer cells to preferentially accumulate radiolabeled choline in cancer tumors, especially prostate cancer tumors, the compounds of the present invention modified with such functional groups are particularly attractive for this purpose. That is, compounds comprising choline analogue, as illustrated in FIG. 4B, may exhibit the same specificity for prostate cancer cells. In this way, the corrole-choline molecule can participate in phosphatidylcholine synthesis. Finally, augmentation of the corrole with monoclonal antibodies (mABs) or chimeric antigen receptors (CARs; antibody fragments) may result in greater targeting. Selective nuclear localization of corroles has been observed in certain prostate cancer cell lines.

As described elsewhere, corroles show therapeutic effects in the absence of further irradiation. Yet further embodiments provide that any of the previously described methods further comprise irradiating the administered compound of claim 1 with energy at a wavelength capable of exciting the molecule to achieve the desired detection or therapeutic effect. Corroles and porphyrins have been shown to be responsive to such irradiation. See, for example, U.S. Pat. Nos. 6,939,963; 6,827,926; and 6,462,192, which are incorporated by reference at least for its discussion of photodynamic therapy, the use of corroles, the methods of applying corroles and other macrocyclic molecules by such methods, and the observed therapeutic effects. While PDT has been described elsewhere in this specification, it should also be appreciated that the irradiation by light of a specific wavelength enables a physician to target specific groups of cells and control the timing and selectivity of treatment. The result of this process is that diseased or unwanted cells are destroyed with less damage to surrounding normal tissues.

The use of radioisotopes or radionuclides, especially those of gallium, provides additional embodiments of the present invention(s). Such embodiments include those methods comprising administering to a patient any of the gallium-based compound disclosed herein, wherein the gallium is an isotope of Ga-67 or Ga-68. These methods may each further comprise measuring the concentration and distribution of the compound in the patient using a radiographic or computed tomography (CT) imaging technique, in particular single photon emission computed tomography (SPECT) in the case where M is Ga-67, or using a positron emission tomography (PET) imaging technique, in the case where M is Ga-68.

Methods of Use—Sterilization Using Sunlight

Metallocorroles and related porphyrin complexes are extremely efficient at generating singlet oxygen. Another potential application using the compounds of the present invention is to use singlet oxygen for applications such as the sterilization of medical equipment or equipment for food/drug/beverage processing, or to kill mold, using the tetrapyrrolic macrocycle and a light source, which might include sunlight, a UV lamp, or the like. There are several established methods for immobilization of a tetrapyrrolic macrocyle that may be used for this application, such as functionalizing $TiO_2$ nanoparticles or other types of particles and painting or spraying or spin-coating them onto a surface.

Flexible antibacterial films of polythiophene-porphyrin polymers are yet another approach. Each of these is considered within the scope of the present invention.

The following listing of embodiments is intended to complement, rather than displace or supersede, the previous descriptions.

Embodiment 1

A compound of Formula (I-H), (I-M), (II-H), or (II-M):

(I-H)

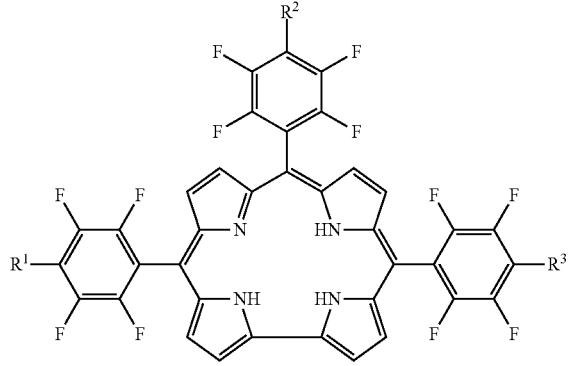

(II-H)

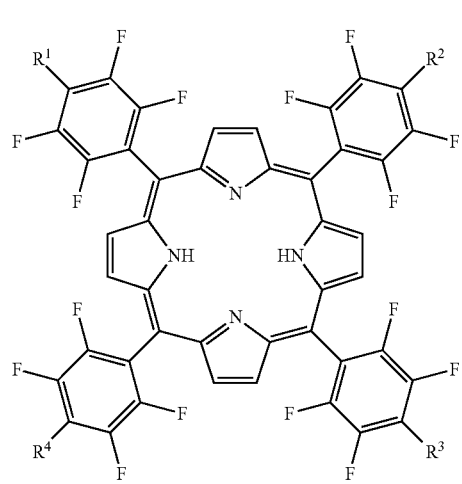

(I-M)

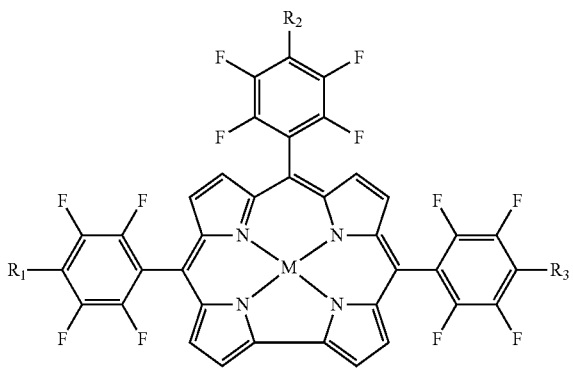

-continued (II-M)

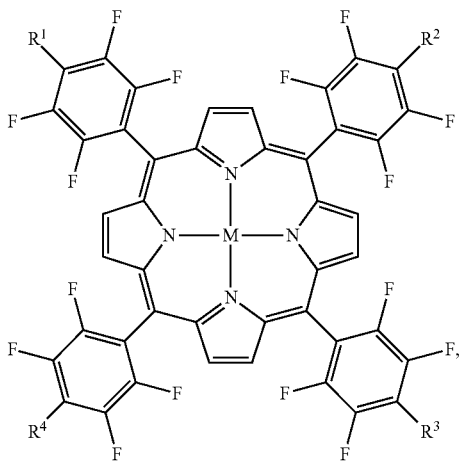

wherein
- $R^1$, $R^2$, $R^3$, and $R^4$ are independently —F or —N(H)—$(CH_2)_m$—Y, provided that at least one of $R^1$, $R^2$, $R^3$, and $R^4$ is —N(H)—$(CH_2)_m$—Y;
- —Y is —$N(Z)_2$, —O—Z, —C(O)—O—Z, —OC(O)Z—, —OC(O)O—Z, —C(O)N(Z)_2, —NH—C(O)—Z, —C(O)NHNH—Z
- —Z is independently $R^5$, —$(CH_2)_m$—X, —$(CH_2)_m$—$OR^5$, —$(CH_2)_m$—$SR^5$, —$(CH_2)_m$—$N(R^5)_2$, —$(CH_2CH_2O)_n$—$OR^5$, —$(CH_2CH_2O)_n$—$N(R^5)_2$, —$(CH_2)_m$—$N_3$, —$(CH_2)_m$—C≡C—$R^5$, an amino acid, peptide, protein, polyol;
- $R^5$ is independently H or $C_{1-12}$alkyl;
- X is Cl, Br, or I;
- m is independently 1-18 (preferably 1-12 or 1-6 or 1-2);
- n is 1-32; and
- M is Ag, Al, Co, Cr, Cu, Fe, Ga, Ge, Hf, Ir, Mo, Mn, Nb, Ni, Os, Pt, Re, Rh, Ru, Sb, Sn, Ta, Ti, V, or W, a lanthanide or actinide, or an isotope or radionuclide thereof, each of which is optionally coordinated to one or more ligands, wherein exemplary ligands are described elsewhere herein.

In some Aspects of this Embodiment, one or more of the macrocyclic ring pyrroles and/or phenyl may also be substituted as described elsewhere herein; e.g., where the macrocyclic ring pyrroles are optionally substituted with one or more carboxylic acid (or carboxylate) or sulfonic acid (or sulfonate) moieties, $X^1$, e.g., where the macrocyclic rings systems are substituted as shown in Structures (I-H"), (II-H"), (I-M"), or (II-M"), or, for example, as shown in the structures shown in FIG. 2 and Complexes 2 and 4 of FIG. 3.

(I-H")

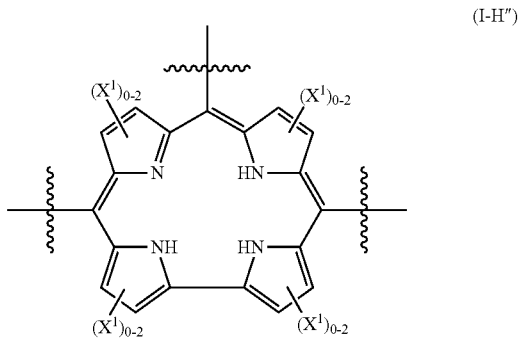

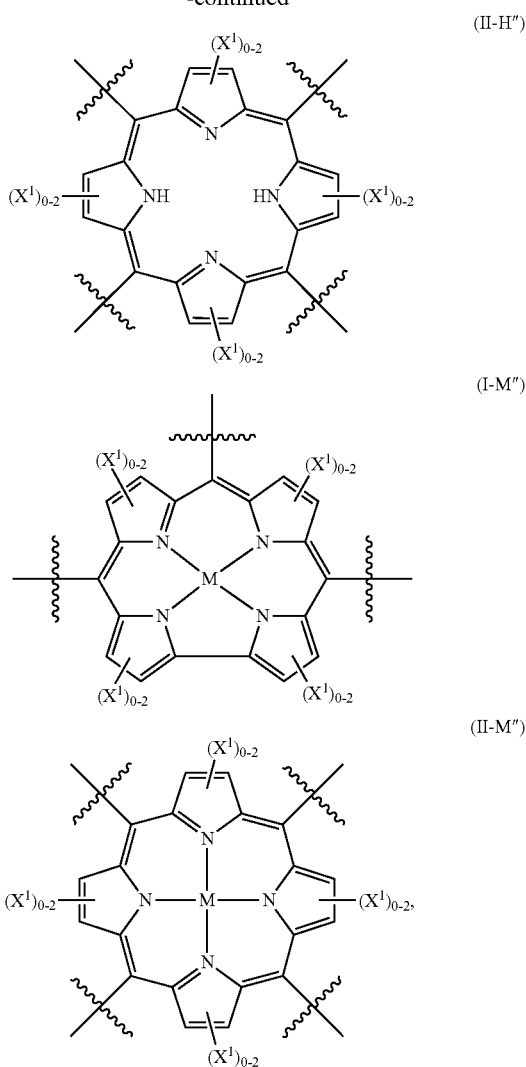

In other Aspects of this Embodiment, the pendant phenyl groups may contain a different array of substituents in place of the fluoro substituents, for example, where $X^2$ is independently H, F, Cl, Br, —CN, optionally fluorinated $C_{1-3}$ alkyl, or optionally fluorinated $C_{1-3}$ alkoxy, as shown in Structure (III), as described elsewhere herein.

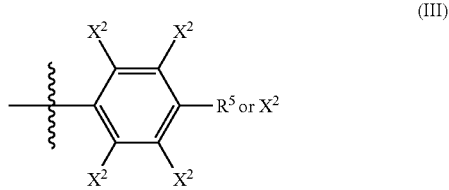

In addition, in certain Aspects of this Embodiment, Z is or comprises a moiety capable of participating in the biorthogonal reactions described herein.

In addition, in certain Aspects of this Embodiment, Z may further chelate or be coordinated to a transition metal compound, for example Pt, as described elsewhere herein. In other Aspects, Z may also conjugate or be bonded to a drug, such as doxorubicin, paclitaxel, or docetaxel, or a fragment thereof. In still other Aspects, Z may be conjugated or be bonded to a nanoparticle, such as carbon nanoparticles (e.g., carbon nanotubes or fullerenes, quantum dots, or nanoparticulate oxides, for example of $TiO_2$).

In addition, in certain Aspects of this Embodiment, Z is, comprises, or is conjugated to a nucleic acid, protein, peptide, amino acid, antibody (including monoclonal antibody), chimeric antigen receptor, transferrin, a ligand for a cellular receptor, or a cellular receptor protein, or alternatively a fragment of an antibody, transferrin, a ligand for a cellular receptor, a cellular receptor protein, or a cell-penetrating peptide, or alternatively a fragment of an antibody, transferrin, a ligand for a cellular receptor, or a cellular receptor protein. Z may also be conjugated to a natural or synthetic polymer or carbohydrate (including naturally or artificially sugar), fat, fatty acid (e.g., oleic or linoleic acid), lipid, glyceride, or vitamin (e.g., folic acid). In other Aspects, Z comprises or is conjugated to glucosamine and/or cell-penetrating peptides.

Embodiment 2

The compound of Embodiment 1, having a Formula (I-H) or (I-M). In related Aspects of this Embodiment, the compound is one having a formula (II-H) or (II-M).

Embodiment 3

The compound of Embodiment 1 or 2, having a Formula (I-M) or (II-M), where M is Al, Cr, Co, Fe, Ga, Mn, Rh, Ru, or Sn. In some Aspects of this embodiment, M has 0, 1, or 2 axial nitrogen donor ligands, for example tertiary or aromatic amine ligands or nitriles, said ligands preferably pyridine or trimethyl amine; include at least trialkyl amines, pyrazine, pyridine, pyrimidine, quinoline, isoquinoline.

Embodiment 4

The compound of any one of Embodiments 1 to 3, having a Formula (I-M) or (II-M), where M is Co, Cr, Fe, Ga, Ir, Mn, Rh, Ru, or Sn. In some Aspects of this embodiment, M has 0, 1, or 2 axial phosphine ligands, for example including triphenyl phosphine ligands.

Embodiment 5

The compound of any one of Embodiments 1 to 4, having a Formula (I-M), where M is Al or Ga, optionally coordinated to one or more ligands.

Embodiment 6

The compound of any one of Embodiments 1 to 5, having a Formula (I-M), where M is Ga(III) having 0, 1, or 2 axial tertiary or aromatic amine ligands.

Embodiment 7

The compound of any one of Embodiments 1 to 6, having a Formula (I-M), where M is Ga(III) having 0, 1, or 2 axial pyridine ligands, preferably one axial pyridine ligand.

Embodiment 8

The compound of any one of Embodiments 1 to 7, wherein one of $R^1$, $R^2$, $R^3$, and $R^4$ is —N(H)—$(CH_2)_m$—Y. In separate Aspects of this Embodiment, two, three, and four of $R^1$, $R^2$, $R^3$, and $R^4$ are —N(H)—$(CH_2)_m$—Y.]

Embodiment 9

A pharmaceutical composition comprising a pharmaceutically acceptable inert ingredient and a compound of any one of Embodiments 1 to 8.

Embodiment 10

The pharmaceutical composition of Embodiment 9, wherein the composition is in a form suitable for local or systemic administration.

Embodiment 11

The pharmaceutical composition of Embodiment 9 or 10, having a Formula (I-M), where M is Al or Ga, optionally coordinated to one or more ligands.

Embodiment 12

The pharmaceutical composition of embodiment 9 or 10, having a Formula (I-M), where M is Ga(III) having 0, 1, or 2 axial tertiary or aromatic amine ligands.

Embodiment 13

The pharmaceutical composition of Embodiment 9 or 10, having a Formula (I-M), where M is Ga(III) having 0, 1, or 2 axial pyridine ligands, preferably one axial pyridine ligand.

Embodiment 14

A method comprising contacting a compound of Formula (I) or Formula (II)

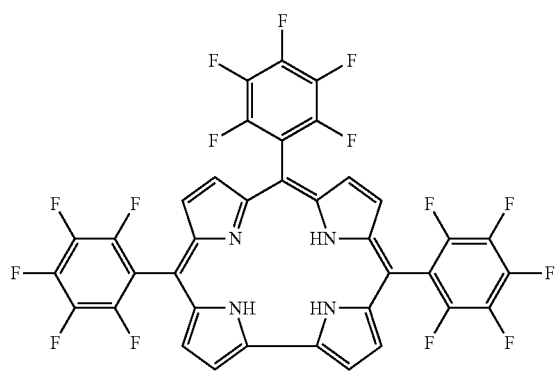
(I)

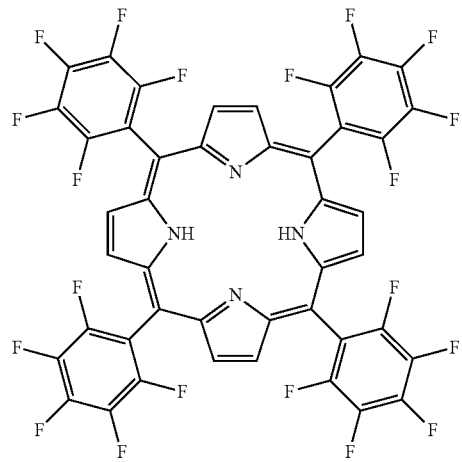
(II)

with a nitrogen nucleophile in the presence of base under conditions to form a compound of Formula (I-H) or (II-H), respectively, so as to form the compound of Formula (I-H) or (II-H),

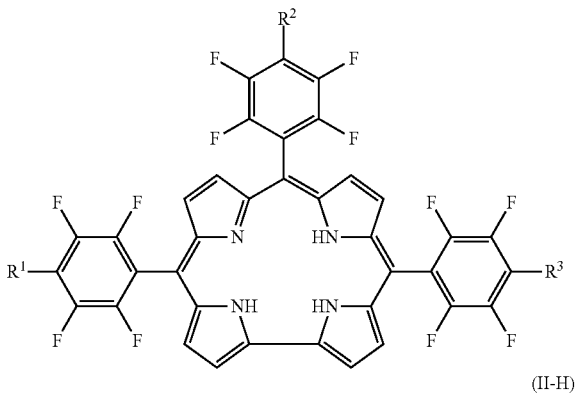
(I-H)

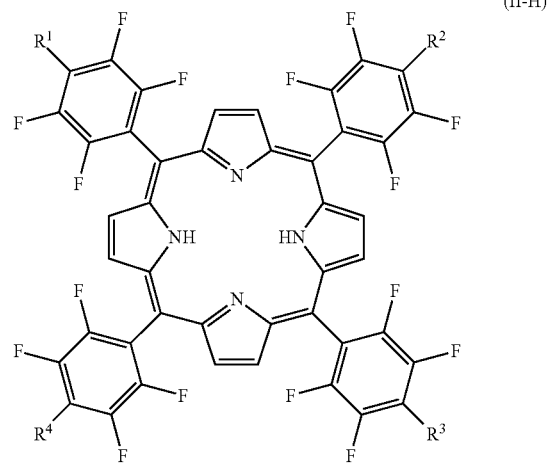
(II-H)

wherein the nitrogen nucleophile is $H_2N$—$(CH_2)_m$—Y, wherein $R^1$, $R^2$, $R^3$, and $R^4$ are independently —F or —N(H)—$(CH_2)_m$—Y, provided that at least one of $R^1$, $R^2$, $R^3$, and $R^4$ is —N(H)—$(CH_2)_m$—Y;

—Y is —N(Z)$_2$, —O—Z, —C(O)—O—Z, —OC(O)Z—, —OC(O)O—Z, —C(O)N(Z)$_2$, —NH—C(O)—Z, —C(O)NHNH—Z

—Z is independently R$^5$, —(CH$_2$)$_m$—X, —(CH$_2$)$_m$—OR$^5$, —(CH$_2$)$_m$—SR$^5$, —(CH$_2$)$_m$—N(R$^5$)$_2$, —(CH$_2$CH$_2$O)$_n$—OR$^5$, —(CH$_2$CH$_2$O)$_n$—N(R$^5$)$_2$, —(CH$_2$)$_m$—N$_3$, —(CH$_2$)$_m$—C≡C—R$^5$, an amino acid, peptide, protein, polyol;

R$^5$ is independently H or C$_{1-12}$alkyl;

X is Cl, Br, or I;

m is independently 1-18 (preferably 1-12 or 1-6 or 1-2) and n is 1-32.

In some Aspects of this Embodiment, one or more of the macrocyclic ring pyrroles and the pendant phenyl groups may also be optionally or alternatively substituted as described elsewhere herein.

In addition, in certain Aspects of this Embodiment, Z is or comprises a moiety capable of participating in the bioorthogonal reactions described elsewhere herein.

In addition, in certain Aspects of this Embodiment, Z may further chelate or be coordinated to a transition metal compound, for example Pt, as described elsewhere herein. In other Aspects, Z may also conjugate or be bonded to a drug, such as doxorubicin, paclitaxel, or docetaxel, or a fragment thereof. In still other Aspects, Z may be conjugated or be bonded to a nanoparticle, such as carbon nanoparticles (e.g., carbon nanotubes or fullerenes), semiconductors or quantum dots, or nanoparticulate oxides (for example comprising SiO$_2$, TiO$_2$, or ZrO$_2$).

In addition, in certain Aspects of this Embodiment, Z is, comprises, or is conjugated to a nucleic acid, protein, peptide, amino acid, antibody (including monoclonal antibody), chimeric antigen receptor, transferrin, a ligand for a cellular receptor, or a cellular receptor protein, or alternatively a fragment of an antibody, transferrin, a ligand for a cellular receptor, a cellular receptor protein, or a cell-penetrating peptide, or alternatively a fragment of an antibody, transferrin, a ligand for a cellular receptor, or a cellular receptor protein. Z may also be conjugated to a natural or synthetic carbohydrate (including naturally or artificial sugar), fat, fatty acid (e.g., oleic or linoleic acid), lipid, glyceride, or vitamin (e.g., folic acid). In other Aspects of this Embodiment, Z comprises or is conjugated to glucosamine and/or cell-penetrating peptides.

Embodiment 15

The method of Embodiment 14, wherein Y is —NH$_2$, —OH, or —C(O)OH.

Embodiment 16

The method of Embodiment 15, further comprising reacting the product of Embodiment 15 with a reagent, wherein:

(a) when Y is —NH$_2$, the reagent is Z—X or Z—C(O)OH, (b) when Y is —OH, the reagent is Z—X, Z—C(O)OH, or Z—OC(O)OH, or (c) when Y is —C(O)OH, the reagent is Z—X, HN(Z)$_2$, or H$_2$NNH—Z, under conditions to form a compound of Formula (I-H) or (II-H), respectively, so as to form the compound of Formula (I-H) or (II-H).

Embodiment 17

The method of any one of Embodiments 14 to 16, further comprising reacting the compound of Formula (I-H) or (II-H), with a precursor compound or salt of Al, Co, Cr, Cu, Fe, Ga, Ge, Ir, Mo, Mn, Os, Pt, Re, Rh, Ru, Sb, Sn, Ti, V, or W, under conditions to produce a compound of Formula (I-M) or (II-M), so as to produce the compound of Formula (I-M) or (II-M)

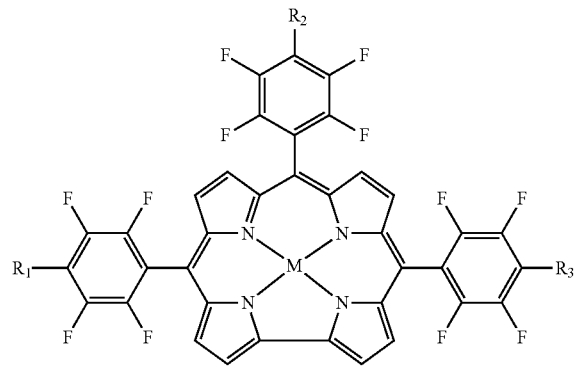

(I-M)

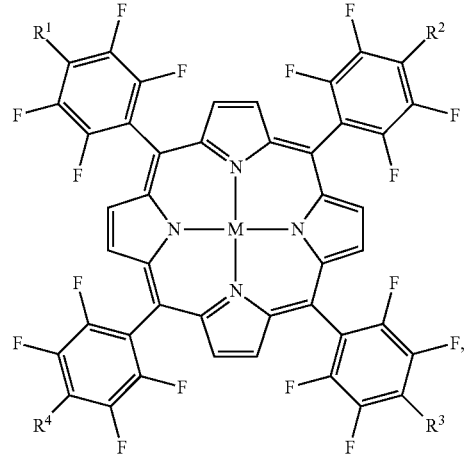

(II-M)

wherein M is Ag, Al, Co, Cr, Cu, Fe, Ga, Ge, Hf, Ir, Mo, Mn, Nb, Ni, Os, Pt, Re, Rh, Ru, Sb, Sn, Ta, Ti, V, or W, a lanthanide or actinide, or an isotope or radionuclide thereof, each of which is optionally coordinated to one or more ligands.

In some Aspects of this Embodiment, one or more of the macrocyclic ring pyrroles and the pendant phenyl groups may also be optionally or alternatively substituted as described elsewhere herein.

Embodiment 18

A method of inhibiting growth factor receptor tyrosine kinase activity, the method comprising administering to a patient in need of such treatment a compound of any one of Embodiments 1 to 8.

Embodiment 19

The method of Embodiment 18, wherein the administration (i) inhibits angiogenesis; (ii) inhibits vascular smooth muscle cell proliferation in disorders selected from the group consisting of atherosclerosis, hyperthrophic heart failure and postsurgical restenosis; (iii) inhibits cell proliferation and migration in the treatment of primary tumors and metastasis; (iv) treats nonmalignant tumors; (v) treats diabetic retinopathy, psoriasis, rheumatoid arthritis, retrolental fibroplasia, macular degeneration, hemangioma, arteriovenous malformation, hypertrophic scars, acne, scleroderma and autoimmune diseases; or (vi) treats bone and cartilage related disorders and inherited skeletal disorders selected from the group consisting of achondroplasia, dwarfism and craniosynostosis.

Embodiment 20

A method of detecting or treating a cardiovascular disease or condition comprising administering a compound of any one of Embodiments 1 to 8 to a patient in need of such treatment.

Embodiment 21

The method of Embodiment 20, wherein the cardiovascular disease or disorder comprises atherosclerosis, congestive heart failure, myocardial infarction, myocardial ischemia, or reperfusion.

Embodiment 22

The method of Embodiment 20 or 21, wherein the compound of claim 1 is one of Formula (I-M) or (II-M)

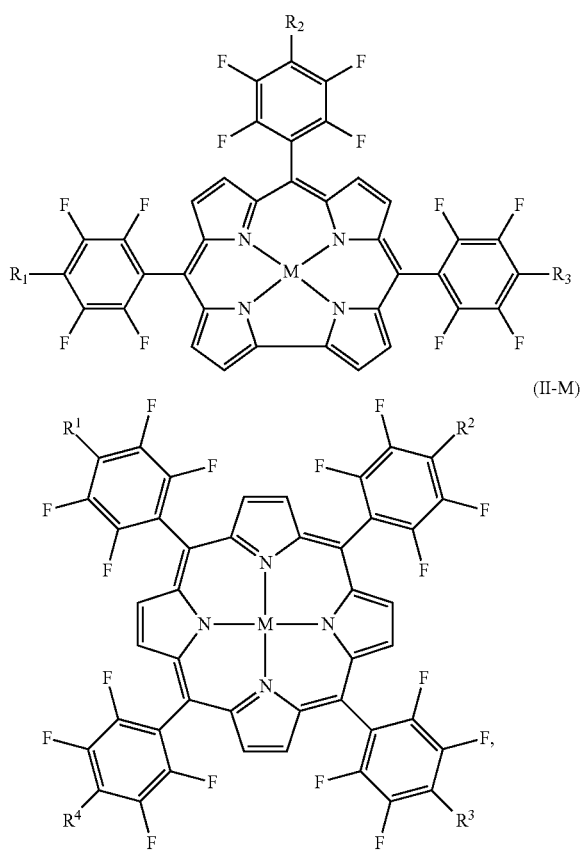

In some Aspects of this Embodiment, one or more of the macrocyclic ring pyrroles and the pendant phenyl groups may also be optionally substituted as described elsewhere herein.

Embodiment 23

The method of Embodiment 22, wherein M is Fe, Ga, or Mn, optionally coordinated to one or more ligands.

Embodiment 24

A method of detecting or treating cancer in a patient, the method comprising administering to a patient known or suspected of being afflicted by cancer a compound of any one of Embodiments 1 to 8.

Embodiment 25

The method of Embodiment 24, wherein the cancer is leukemia, lung cancer, colon cancer, CNS cancer, melanoma, ovarian cancer, renal cancer, prostate cancer, or breast cancer.

Embodiment 26

The method of Embodiment 24 or 25, wherein the compound is a compound of Formula (I-M).

Embodiment 27

The method of any one of Embodiments 24 to 26, wherein the compound is a compound of Formula (I-M), where M is Al or Ga, optionally coordinated to one or more ligands.

Embodiment 28

The method of any one of Embodiments 24 to 26, wherein the compound is a compound of Formula (I-M), where M is Ga(III) having 0, 1, or 2 axial tertiary or aromatic amine ligands.

Embodiment 29

The method of any one of Embodiments 24 to 26, wherein the compound is a compound of Formula (I-M), where M is Ga(III) having 0, 1, or 2 axial pyridine ligands, preferably one axial pyridine ligand.

Embodiment 30

The method of any one of Embodiments 24 to 29, wherein the compound is a compound of Formula (I-M), wherein one of $R^1$, $R^2$, $R^3$, and $R^4$ is —N(H)—(CH$_2$)$_m$—Y.

Embodiment 31

The method of any one of Embodiments 24 to 30, further comprising irradiating the administered compound of any one of Embodiments 1 to 8 with energy at a wavelength capable of exciting the molecule to achieve the desired detection or therapeutic effect.

Embodiment 32

The method of any one of Embodiments 24 to 31, wherein the detecting or treating comprises detecting.

Embodiment 33

The method of Embodiment 32, wherein the detecting comprises imaging.

Embodiment 34

The method of any one of Embodiments 24 to 31, wherein the detecting or treating comprises treating. In certain Aspects of this Embodiment, treating is done on patient exhibiting the disease or condition. In other Aspects of this Embodiment, treating is done prophylactically on a patient as risk of the disease or condition.

Embodiment 35

A method comprising administering to a patient a compound of any one of Embodiments 1 to 8, having a Formula of (I-M), wherein M is Ga-67 or Ga-68.

Embodiment 36

The method of Embodiment 35, further comprising measuring the concentration and distribution of the compound in the patient using a radiographic or computed tomography (CT) imaging technique, in particular single photon emission computed tomography (SPECT) in the case where M is Ga-67, or using a positron emission tomography (PET) imaging technique, in the case where M is Ga-68.

EXAMPLES

The following Examples are provided to illustrate some of the concepts described within this disclosure. While each Example is considered to provide specific individual embodiments of composition, methods of preparation and use, none of the Examples should be considered to limit the more general embodiments described herein.

In the following examples, efforts have been made to ensure accuracy with respect to numbers used (e.g. amounts, temperature, etc.) but some experimental error and deviation should be accounted for. Unless indicated otherwise, temperature is in degrees Celsius, pressure is at or near atmospheric.

Example 1. General Methods

Example 1.1. Synthesis of Gallium Corroles

Generally, synthesis of the tetrapyrrolic scaffold can be accessed through a direct route by condensation of an optionally substituted aryl aldehyde and optionally substituted pyrrole. Synthesis of the corrole scaffold is further followed by oxidation by dichlorodicyanobenzoquinone (DDQ). Such a synthesis yielded grams of the purified tris(pentafluorophenyl)corrole (tpfc) framework in a few hours. Gallium insertion required only one additional step after the initial reaction; this proceeds in nearly quantitative yield using standard techniques Complex 1 (Bendix J, et al., *Angew Chem Int Ed Engl* 39(22) 4048-4051 (2000), Complex 2 (Saltsman I, et al. (2002) *J Am Chem Soc* 124(25):7411-7420), and Complex 4 (Saltsman I, Goldberg I, Gross Z (2003), *Tetrahedron Lett* 44(30):5669-5673) were obtained via literature methods, and molecular masses were confirmed by MALDI-TOF mass spectrometry (FIG. 3). The amino-caproate-substituted corrole Complex 3 was synthesized in 37% yield by nucleophilic aromatic substitution of a para-fluoro substituent on the pentafluorophenyl ring of Complex 1 with a sub-stoichiometric amount of 6-aminocaproic acid in anhydrous dimethyl sulfoxide (DMSO) with 1% anhydrous pyridine at 100° C. The reactions were highly selective in that only the parafluoro substituent undergoes substitution. Although preparation of Complex 4 required phosgene and could only be performed on the metallated corrole, Complex 3 could be synthesized using either metallated or free base corrole and did not require harsh reagents.

The optimized conditions for an orthogonal functionalization reaction reported herein, the nucleophilic aromatic substitution at the para-position of one of the pentafluorophenyl rings with substoichiometric 6-aminocaproic acid allows convenient access to large quantities of the carboxylated corrole Complex 3, and a range of derivatives therefrom. In this work, it was observed that both the temperature and identity of the nucleophile had a profound effect on the yield. Primary amines terminated by carboxylic acids proved the most efficient under elevated temperatures. Aminocaproic acid is inexpensive, non-toxic and when used in excess, results in three products (monocarboxylate (20%); dicarboxylate (72%); and triscarboxylate (9%)), which can easily be separated. Other amines were tested but were of limited success due to lower nucleophilicity or resulted in multiple products. In addition, the nucleophilic aromatic substitution must be performed at elevated temperature (typically in a range of from about 80° C. to about 150° C., preferably about 100° C.), therefore, only nucleophiles such as aminocaproic acid which can sustain such temperatures are optimal.

Figure 5:
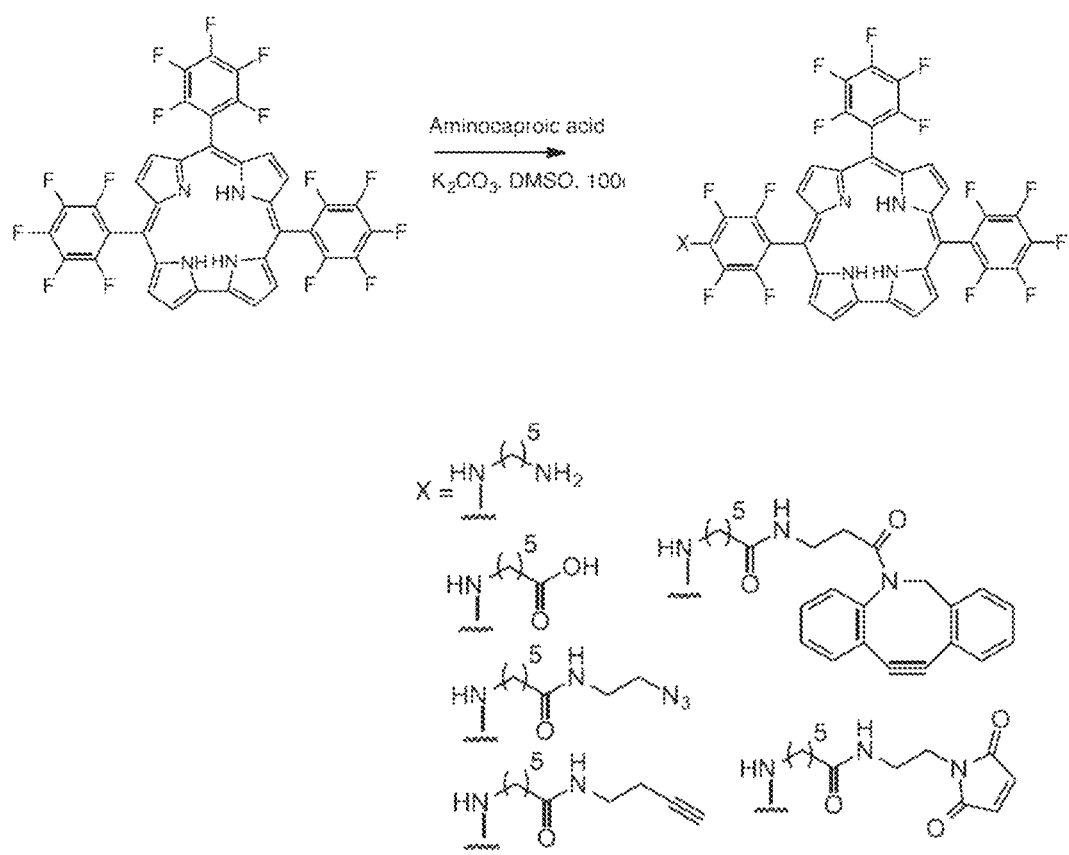
FIG. 5 shows an exemplary three-step synthetic route to access click and Staudinger functional groups on the corrole framework.

The strategies for further modification of the corrole framework to access functional groups important for cancer treatment are outlined in FIGS. 4B and 5. Some test reactions of the two-step amide bond formation reaction in FIG. 4B were conducted and consistently achieved >65% isolated yield. The ability to install all of the click and Staudinger groups shown in FIG. 5 has also been demonstrated as exemplary complexes. An illustration of the efficacy of the three-step approach is the synthesis of a strained cyclooctyne-functionalized corrole through the amide bond formation of the carboxylated corrole with a dibenzocyclooctyne amine. With 7.5% overall yield, the carboxylated corrole can be considered synthetically valuable. Direct nucleophilic aromatic substitution of the dibenzocyclooctyne-amine at 100° C. resulted in decomposition rather than the desired product. However, coupling to the carboxylated corrole proceeds in 71% yield. While only 5% overall yield for the three reactions, the lowest yielding reaction, formation of the tpfc framework, can be prepared in gram quantities, therefore the functionalization steps are above 50% yield.

More specifically, Complex 3 is a promising candidate for both imaging applications and potential development as a chemotherapeutic, as it is easily solubilized in water, and easily prepared and purified. The synthesis and characterization of Complex 3 (FIG. 4A) proceeded as follows: a round-bottom flask was charged with Complex 1 (20.0 mg, 0.025 mmol), 6-aminocaproic acid (3.1 mg, 0.024 mmol), and $K_2CO_3$ (18.0 mg, 0.13 mmol) under argon. To this mixture was added anhydrous DMSO (0.5 mL) and anhydrous pyridine (1%). The reaction mixture was heated to 100° C. and stirred for 18 h, after which it was cooled and then diluted with $CHCl_3$ (10 mL), washed sequentially with $H_2O$ (4×10 mL) and brine (1×10 mL), and then dried over $Na_2SO_4$. The solvent was removed in vacuo, and the crude residue was purified by flash chromatography [$SiO_2$, 1% pyridine, 0-10% (vol/vol) MeOH in $CH_2Cl_2$] to provide 9.1 mg (37%) of monocarboxylate as a purple solid. Characterization of Complex 3 was performed using $^1H/^{19}F$ NMR spectroscopy and MALDI-TOF mass spectrometry, although these techniques did not distinguish between regioisomers with mono-substitution at the 5-, 10-, or 15-fluoro position. $^1$H NMR (300 MHz, CDCl$_3$) δ 9.11-9.03 (m, 2H), 8.88-8.63 (m, 2H), 8.58-8.53 (m, 4H), 3.69-3.64 (m, 2H), 2.49-2.45 (t, J=6.2 Hz, 2H), 1.87-1.75 (m, 2H), 1.67-1.55 (m, 2H), 0.91-0.85 (m, 2H); $^{19}$F NMR (282 MHz, CDCl$_3$) δ −137.17, −137.23, −137.69, −137.72, 140.11, −141.69, −152.66, −152.97, −153.14, −160.54, −160.60, −161.63, −162.03, −162.91. MALDI-TOF m/z calculated for C$_{43}$H$_{20}$F$_{14}$GaN$_5$O$_2$ [M$^+$H]$^+$: 974.065. found: 974.126. UV-Vis (DMSO): λmax (e) 420 nm (130,300 M$^{-1}$·cm$^{-1}$).

The gallium corroles were solubilized in DMSO, and concentrations were determined by UV-Vis using calculated extinction coefficients: (Complex 1) $\varepsilon_{420\ nm}$=284,000 cm$^{-1}$·M$^{-1}$, (Complex 2) $\varepsilon_{424\ nm}$=74,700 cm$^{-1}$·M$^{-1}$, (Complex 3) $\varepsilon_{420\ nm}$=130,300 cm$^{-1}$·M$^{-1}$, (Complex 4) $\varepsilon_{426\ nm}$=130,000 cm$^{-1}$·M$^{-1}$ (FIG. 3). Stock solutions were stored in the dark at room temperature before use.

Example 1.2

Reagents were obtained from the indicated suppliers: HBSS without phenol red and trypsin-EDTA (0.25%), Invitrogen/Gibco; PBS, Mediatech; 4',6-diamidino-2-phenylindole dihydrochloride (DAPI) and DMSO, Sigma-Aldrich; paraformaldehyde, Electron Microscopy Sciences; WGA, Alexa Fluor 488 conjugate, Invitrogen/Molecular Probes; and ProLong Gold Antifade Mountant with DAPI, Life Technologies. Human Cancer Cell Lines. Four cell lines from the NCI60 cell panel (Shoemaker RH (2006) The NCI60 human tumour cell line anticancer drug screen. *Nat Rev Cancer* 6(10):813-823) representing four distinct tumor types were used in this study: DU-145, prostate; MDA-MB-231, breast; SK-MEL-28, melanoma; and OVCAR-3, ovarian. Cells were grown in RPMI 1640 cell culture medium (Mediatech) containing 2 mM L-glutamine, supplemented with 10% FBS (Omega Scientific), and maintained at 37° C. under 5% CO$_2$ in a humidified incubator.

Example 1.3. MTS Assay

Cells (DU-145, MDA-MB-231, SK-MEL-28, and OVCAR-3) were seeded in 96-well microtiter plates (5×103 cells per well; 0.09 mL per well) 24 h before the addition of corroles. At the time of drug treatment, stock solutions of 1-4 were diluted to 10-fold the desired final test concentrations with RPMI medium 1640. Aliquots of 10 pt of these diluted solutions were added to the appropriate microtiter wells containing 90 μL of medium, resulting in the required final drug concentrations (eight concentrations per compound, ranging from 0.3 to 600 μM). The final concentration of DMSO in test culture was <1%. All cells were incubated in the dark throughout the 72-h exposure period and did not receive prolonged exposure to light. Following 72 h of exposure at 37° C., cell viability was determined using the MTS assay (CellTiter 96 Aqueous One Cell Proliferation Assay; Promega) according to the manufacturer's instructions. Absorbances were measured using a microplate reader (Synergy 4; Biotek Instruments) at 490 nm. Experiments were performed in triplicate and each dose-response curve represents the mean of three or more independent experiments. Spectrophotometric data were analyzed by sigmoid dose-response, nonlinear regression analysis; the IC50, E$_{max}$ values, and associated SE were calculated using GraphPad Prism 6 (GraphPad Software).

Example 1.4. Confocal Imaging of Intracellular Gallium Corroles

Confocal images were obtained for DU-145, MDA-MB-231, SK-MEL-28, and OVCAR-3 cells exposed to 3 μM 1, 2, 3, or 4 for 3 h at 37° C., 5% CO$_2$ in the dark using an upright LSM510 2-Photon microscope (Carl Zeiss Micro-Imaging). Protocols for seeding cells, immunolabeling, and confocal image acquisition were as previously described.

Example 1.5. Uptake of Gallium Corroles. (FIG. 1)

The intracellular uptake of gallium corroles was quantified using the ImageXpressultra laser point-scanning confocal microscope (Molecular Devices). The fluorescence image acquisition settings were as previously reported (Lim P, et al. (2012), *Chem Res Toxicol* 25(2):400-409.). Cells (DU-145, SK-MEL-28, MDA-MB-231, and OVCAR-3) were seeded in 96-well dishes (8×103 cells per well in 0.1 mL) and allowed to attach overnight. Complex 1, 2, 3, or 4 was added directly to cell media at 30 μM final concentration or media only control, and incubated for 0.25, 1, 3, or 24 h at 37° C. in the dark under a 5% CO$_2$ atmosphere. Cells were fixed and labeled in situ with WGA-Alexa Fluor 488 conjugate and DAPI to allow for the identification of cell boundary and nucleus, respectively. The quantification of blue (DAPI) fluorescence signals in each sample yielded the total number of cells in that population. Corresponding determination of red (corrole) fluorescence within each cell, corrected for background fluorescence from untreated cells, provided the number of cells containing corroles. For each corrole concentration at various time points, fluorescence data were obtained for 1,000-22,000 individual cells. Data acquisitions and analyses were performed as described (Lim P, et al. (2012), *Chem Res Toxicol* 25(2):400-409). The percentage of corrole-positive cells and the median fluorescence intensity (median RFU) for each treatment were plotted in a three-axis graph using Microsoft Office Excel 2007 (Microsoft Corporation).

Example 1.6. NCI60 Anticancer Drug Screen

The aminocaproate-substituted corrole Complex 3 was submitted to NCI for cytotoxic screening at a single high dose (10−5M) in a panel of 60 human tumor cell lines (NCI60). Details of the cytotoxicity assessment in the NCI anticancer drug screen have been described previously, in Monks A, et al. (1991) Feasibility of a high-flux anticancer drug screen using a diverse panel of cultured human tumor cell lines. *J Natl Cancer Inst* 83(11):757-766, this reference being incorporated by reference for these teachings.

Example 2. Overview Results

Derivatives of gallium(III) tris(pentafluorophenyl)corrole, [Ga(tpfc)] (Complex 1), with either carboxylic acids (Complexes 3 and 4) or sulfonic acid (Complex 2) as macrocyclic ring substituents: the aminocaproate derivative, Complex 3 [Ga(5-ACtpfc)], demonstrated high cytotoxic activity against all NCI60 cell lines derived from 9 tumor types and confirmed very high toxicity against melanoma cells, specifically the LOX IMVI and SK-MEL-28 cell lines. As described below, the toxicities of these Ga-corrole complexes showed cytotoxicity across a range of cancers, including prostate (DU-145), melanoma (SK-MEL-28), breast (MDA-MB-231), and ovarian (OVCAR-3) cancer cells. Confocal fluorescence imaging revealed facile uptake of functionalized gallium corroles by all human cancer cells that followed the order: 4>>3>2>>1 (intracellular accumulation of gallium corroles was fastest in melanoma cells). These carboxylated gallium corroles showed promise as chemotherapeutics with the advantage that they also can be employed for tumor imaging.

Further, the present inventors have identified proteins and protein-protein assemblies of great interest as targets in ovarian cancer and have previously studied the role of the porphyrin group in metalloprotein folding at elevated temperature (MAP graduate work) and protein-protein interactions using microfluidic systems.

Example 3. Modulation of Cytotoxicity by Substituents on the Corrole Ring

The effects of bis-sulfonate, carboxylate, and aminocaproate ring substituents on gallium corrole cytotoxicities were examined using four human cancer cell lines, representing tumors of different origin selected based on previously described sensitivities. Each cell line, DU-145 (prostate), SK-MEL-28 (melanoma), MDA-MB-231 (breast), or OVCAR-3 (ovarian), was incubated in growth medium with varying concentrations of 1-4 at 37° C. for 72 h in the dark, and the cytotoxicity as a function of concentration was measured using the MTS assay. Dose-response curves are shown in FIGS. 6A-D.

$IC_{50}$ values ranged from 4.8 to 17.6 µM with carboxylated corrole Complexes 3 and 4; these corroles had the highest anticancer activities against all cell lines (FIGS. 6C-D and Table 1). In particular, Complex 4 displayed promising activity against the SK-MEL-28 melanoma line, with an $IC_{50}$ value of 4.8 µM. The cytotoxicities of the carboxylated corroles toward all cell lines were nearly identical, except for Complex 4 in SK-MEL-28 cells, with $IC_{50}$ values in the range of 10-20 µM (FIG. 6D and Table 1), or about 10-fold lower against the same cell lines relative to Complexes 1 and 2. With the exception of the activity of Complex 1 against SK-MEL-28 and OVCAR-3 cell lines, with $IC_{50}$ values of 61.3 and 58.1 µM, respectively (Table 1), the $IC_{50}$ values of Complexes 1 and 2 had values ranging from 100 to 274 µM. The order of magnitude improvement in $IC_{50}$ against SK-MEL-28 results from substitution with a single carboxylic acid at the 3 position of Complex 1, lowering the $IC_{50}$ of 4 to 4.8 µM (FIG. 3 and Table 1). Against the prostate cancer cell line DU-145, bis-sulfonated Complex 2 displayed an $IC_{50}$ of 159 µM, whereas the carboxylated analog Complex 4 was ~12-fold lower (12.9 µM). In general, the bis-sulfonated corroles were the least effective against all tested cell lines, with the lowest observed $IC_{50}$ values (~130 µM) against the melanoma line SK-MEL-28 and breast cancer cell line MDA-MB-231. This finding contrasts with that for monocarboxylated Complexes 3 and 4 corroles, which displayed $IC_{50}$ values of <20 µM against all cell lines tested, with markedly good activities against SK-MEL-28 and OVCAR-3 lines. The mean $IC_{50}$ values for all carboxylated corroles (12.8±1.3 µM) revealed twofold to threefold higher potency than that reported for cisplatin [46.4±12.4 µM and 39 µM] in MDA-MB-231 cells. Although the $IC_{50}$ values were similar for the carboxylated Ga(III) corroles, data in Table 1 suggest that Complex 4 possesses somewhat greater potency relative to aminocaproate analog Complex 3.

TABLE 1

Dose-response parameters for gallium corroles

| Complex | Cells* | $IC_{50}$† | ±SE |
|---|---|---|---|
| 1 | DU-145 | 134.6 | 10.9 |
|   | SK-MEL-28 | 61.3 | 9.9 |
|   | MDA-MB-231 | 100.8 | 6.8 |
|   | OVCAR-3 | 58.1 | 7.2 |
| 2 | DU-145 | 158.9 | 16.2 |
|   | SK-MEL-28 | 131.4 | 18.5 |
|   | MDA-MB-231 | 129.2 | 13.2 |
|   | OVCAR-3 | 274.2 | 15.5 |
| 3 | DU-145 | 17.6 | 0.8 |
|   | SK-MEL-28 | 14.4 | 0.7 |
|   | MDA-MB-231 | 13.7 | 1.0 |
|   | OVCAR-3 | 12.7 | 0.6 |
| 4 | DU-145 | 12.9 | 0.5 |
|   | SK-MEL-28 | 4.8 | 0.3 |
|   | MDA-MB-231 | 15.3 | 2.0 |
|   | OVCAR-3 | 11.1 | 0.4 |

*Human cancer cells were exposed to each complex for 72 hrs. Data represent the mean of three separate experiments
†$IC_{50}$ values are reported in micromolar concentration

Example 4. Uptake of Ga(tpfc) Derivatives

The intense fluorescence of gallium corroles was exploited to examine intracellular accumulation using confocal microscopy and ImageXpressultra analysis to measure the rate of uptake of differentially substituted derivatives across all cell lines. Avidity of cellular uptake can influence the observed cytotoxicity of corroles. Confocal image analysis was performed on DU-145 (prostate), SK-MEL-28 (melanoma), MDA-MB-231 (breast), or OVCAR-3 (ovarian) cells incubated with 3 µM Complexes 1, 2, 3, or 4 in complete or unsupplemented media for 3 h in the dark; representative images are shown in FIG. 1. The nuclei and plasma membranes of cells were visualized by labeling with DAPI (blue fluorescence) and wheat germ agglutinin (WGA)-Alexa Fluor 488 conjugate (green fluorescence), which bind to nuclear DNA and N-acetylglucosamine, respectively. Gallium corroles were readily observable in situ as red fluorescence of varying intensities in cells treated with Complexes 1, 2, 3, or 4; in contrast, red fluorescence was absent in untreated cells. In cells treated with 3 µM Complex 1 for 3 h, red fluorescence was not apparent (data not shown), whereas analysis of cellular uptake kinetics revealed that less than 5% of cells were able to internalize Complex 1 at this time point. The intensities of red fluorescence were much greater in cells exposed to Complexes 2 and 4 compared with Complex 3, even though the $IC_{50}$ of Complex 3 was about the same as Complex 4 and 10-fold lower than Complex 2 (Table 1). The standard curves of corrole fluorescence versus compound concentration generated for Complex 1 and its derivatives differed significantly, most likely owing to differences in quantum yields, absorption cross-sections, and solubilities; these data confirmed that fluorescence intensity measurements cannot be used to predict or directly compare the intracellular concentrations of different gallium corroles. However, the relative intracellular concentrations of a single compound can be assessed by its fluorescence intensity and compared among different cell lines. Data obtained from confocal image analysis verified that intracellular uptake of Complexes 1-4 can be monitored by fluorescence microscopy for all cell lines tested.

To quantify the kinetics of intracellular uptake and accumulation of each derivative, ImageXpressultra, a laser point-scanning confocal microscope, was used for analyses. Cellular uptake of Complexes 1-4 was assessed in human cancer cell lines DU-145 (prostate), SK-MEL-28 (melanoma), MDA-MB-231 (breast), or OVCAR-3 (ovarian) at a final concentration of 30 µM. Cells were incubated at 37° C. in the dark for 0.25, 1, 3, or 24 h. Again, functional group substitution of Complex 1 resulted in significant differences in the rate of uptake, as follows: Complexes 4>>3>2>>1. Within 15 min, Complex 4 fluorescence was observable in ~80% of ovarian cancer cells, 97% of breast cancer cells, and >99% of prostate cancer and melanoma cells, whereas up to 3 and 24 h were required to label >80% of cells from all four cancer lines with Complexes 3 and 2, respectively. For Complex 1, significant uptake (≥80% cells) in melanoma, ovarian, and breast cancer cell lines required 24 h. The uptake of Complex 1 was quite slow in prostate cancer cells.

Intracellular accumulation, which correlates with the median RFU, was compared among the four human cancer cell lines and revealed the most efficient uptake of Complexes 1-4 into melanoma (SK-MEL-28) cells. After 3 h of incubation, the fluorescence of Complex 4 was approximately twofold to threefold higher in melanoma cells compared with prostate, breast, and ovarian cancer cells. A twofold enhancement of fluorescence in melanoma cells compared with the other three cell lines was observed for Complexes 1,2, and 3 after 24 h. The most efficient uptake of gallium corroles into melanoma (SK-MEL-28) cells has been proposed to be consistent with transferrin-mediated transport, because these cells are well known to avidly accumulate iron via this mechanism. The exceptional efficiency of gallium corrole uptake and intracellular accumulation in melanoma cells correlates with an observable increase in cytotoxic activity against these cells over other cell lines for Complexes 1 and 4 (FIG. 6 and Table 1); but for Complexes 2 and 3, the cytotoxic activity is similar among all cell lines and does not correlate with the accumulated corrole levels (FIG. 6 and Table 1). Overall, excellent kinetics of intracellular uptake and accumulation, especially in melanoma cells, were found for Complexes 3 and 4, suggesting that substitution with carboxylic acid or aminocaproic acid increases cell permeability.

Example 5. Profile of Complex 3 [Ga(ACtpfc)] Sensitivity in a NCI60 Cell Panel

Figure 7:
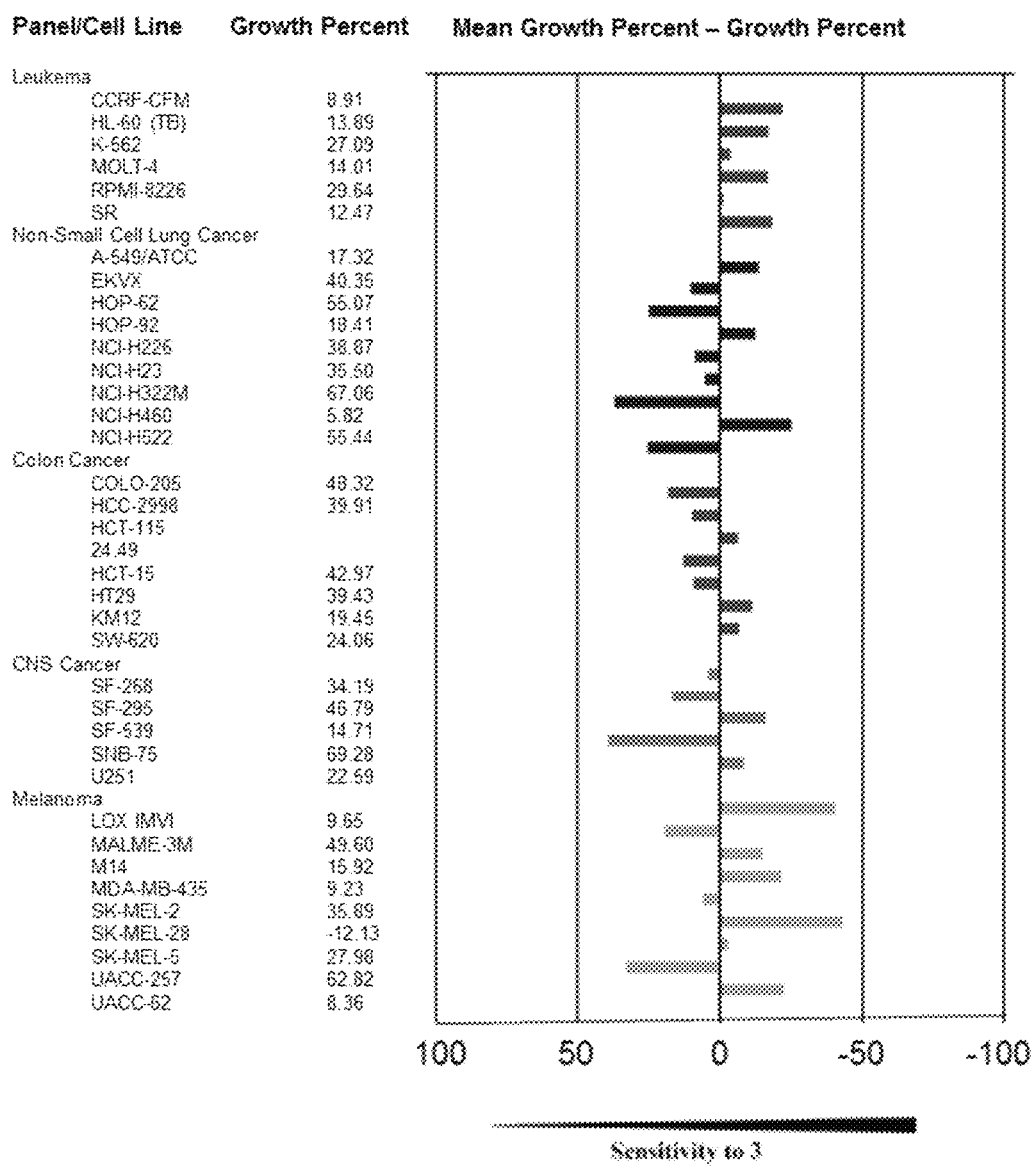
FIG. 7 shows mean graph representation of growth inhibition effects of Complex 3 [Ga(ACtpfc)]. Carboxylated gallium corrole submitted to the NCI screen were evaluated against 60 human tumor cell lines. Growth percent and lethality were obtained at a single dose (10−5 M) of 3 and the mean growth percent across all 60 cell lines was calculated. The individual response of each cell line to the compound is depicted by a bar graph extending either to the right or left of the mean. Bars projecting to the right represent cell lines that are more sensitive than average, whereas less sensitive cell lines show bars projecting to the left. The length of each bar is proportional to the relative sensitivity compared with the mean determination. The graph was color-coded by tissue of origin: red, leukemia cell line; blue, lung cancer; green, colon cancer; gray, CNS cancer; coral, melanoma; purple, ovarian cancer; gold, renal cancer; turquoise, prostate cancer; pink, breast cancer.
Figure 7:
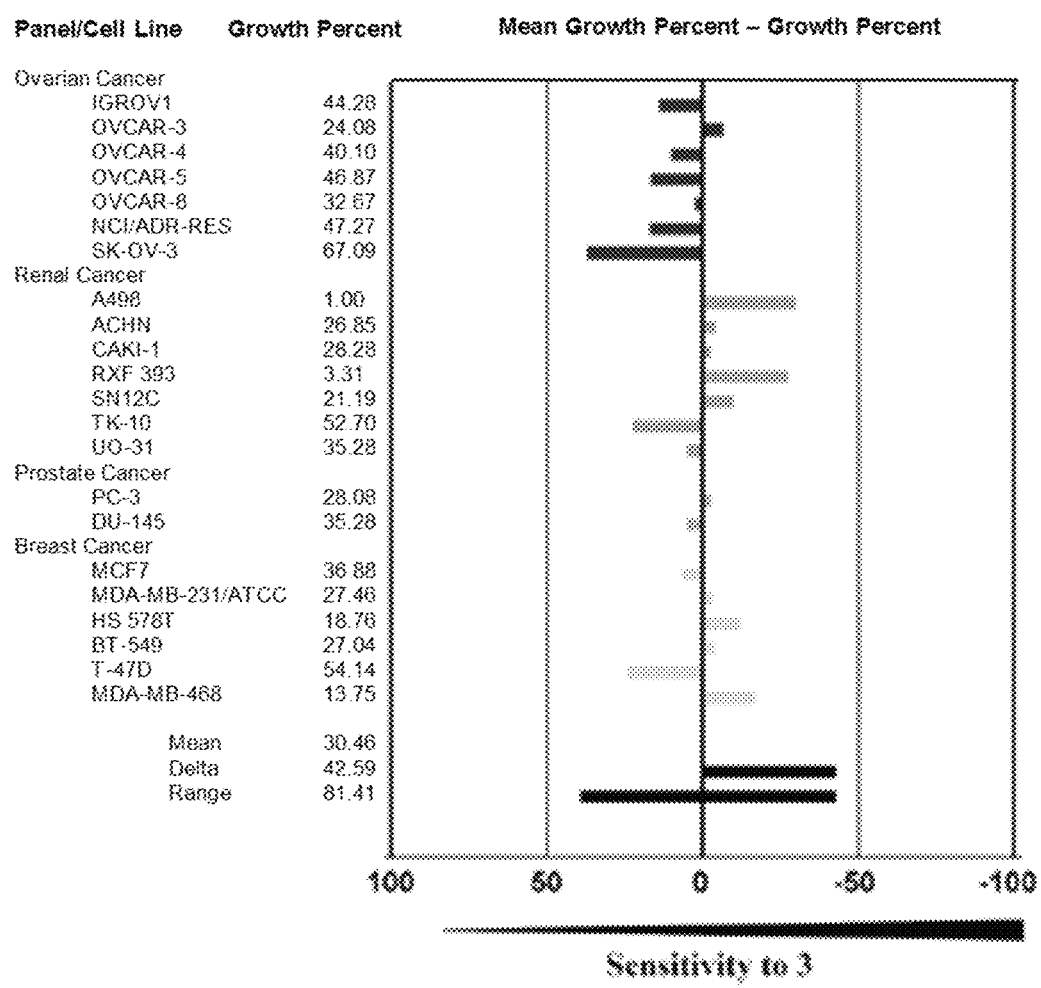

In view of the promising results observed for carboxylated corroles, Complex 3 was selected for expanded cell screening to uncover additional susceptible cancer cell lines. The cytotoxic activity of Complex 3 was tested at a dose of $10^{-5}$ M against 60 human cancer cell lines representing nine distinct tumor types in the anticancer screening program of the National Cancer Institute (NCI). The in vitro parameters for cytotoxicity, growth percent, and lethality were obtained for Complex 3 and reported as a mean graph of the percent growth of treated cells (FIG. 7). Bars in the mean graph depict the deviation of individual tumor cell lines from the overall mean value for all cells tested. Bars that project to the right of the mean represent cell lines that are more sensitive to Complex 3, whereas cell lines less sensitive to the compound display bars that project to the left.

The numerical values associated with this assay represent growth relative to the no-drug control and the numbers of cells at time 0 (FIG. 7). This allows detection of both growth inhibition (values between 0 and 100) and lethality (values less than 0). For example, a value of 100 signifies no growth inhibition, 40 means 60% growth inhibition, 0 means no net growth over the course of the experiment, −40 means 40% lethality, and −100 indicates all cells are dead. The percentage of growth inhibition and lethality resulting from Complex 3 is given in Table 2. In most cell lines, inhibition of cell proliferation was observed ranging from 30% to 99% following exposure to 10 µM 3 for 48 h, with an average growth inhibition of 70%. Growth inhibitions reflect cytostatic activity of the compound as previously shown for Complex 2. In contrast, cell lethality is only evident in melanoma cells, specifically the LOX IMVI and SK-MEL-28 cell lines. Overall, Complex 3 was highly active against all NCI60 cell lines derived from nine tumor types (Table 2), suggesting that carboxylated gallium corroles are effective, cell-permeable chemotherapeutic agents.

TABLE 2

Cytotoxicity of Complex 3 in NCI60 cell panel

| Cell line | Growth inhibition, % | Cell line | Growth inhibition, % |
|---|---|---|---|
| Leukemia | | Melanoma | |
| CCRF-CEM | 91.1 | LOX IMVI | 9.7** |
| HL-60 (TB) | 86.1 | MALME-3M | 50.4 |
| K-562 | 72.9 | M14 | 84.1 |
| MOLT-4 | 86.0 | MDA-MB-435 | 90.8 |
| RPMI-8226 | 70.2 | SK-MEL-2 | 64.1 |
| SR | 87.5 | SK-MEL-28 | 12.1** |
| Non-small-cell lung cancer | | SK-MEL-5 | 72.0 |
| | | UACC-257 | 37.2 |
| A549/ATCC | 82.7 | UACC-62 | 91.6 |
| EKVX | 59.7 | Ovarian Cancer | |
| HOP-62 | 44.9 | IGROV1 | 55.7 |
| HPO-92 | 81.6 | OVCAR-3 | 75.9 |
| NCI-H226 | 61.1 | OVCAR-4 | 59.9 |
| NCI-H23 | 64.5 | OVCAR-5 | 53.1 |
| NCI-H322M | 32.9 | OVCAR-8 | 67.3 |
| NCI-H460 | 94.2 | NCI/ADR-RES | 52.7 |
| NCI-H522 | 44.6 | SK-OV-3 | 32.9 |
| Colon cancer | | Renal Cancer | |
| COLO 205 | 51.7 | A498 | 99.0 |
| HCC-2998 | 60.1 | ACHN | 73.2 |
| HCT-116 | 75.5 | CAK-1 | 71.7 |
| HCT-15 | 57.0 | RXF 398 | 96.7 |
| HT29 | 60.6 | SN12C | 78.8 |
| KM12 | 80.6 | TK-10 | 47.3 |
| SW-620 | 75.9 | UO-31 | 64.7 |
| CNS Cancer | | Breast Cancer | |
| SF-268 | 65.8 | MCF7 | 63.1 |
| SF-295 | 53.2 | MDA-MB-231/ATCC | 72.5 |
| SF-539 | 85.3 | HS 578T | 81.2 |
| SNB-75 | 30.7 | BT-549 | 73.0 |
| U251 | 77.4 | T-47D | 45.9 |
| Prostate Cancer | | MDA-MB-468 | 86.3 |
| PC-3 | 71.9 | | |
| DU-145 | 64.7 | | |

**Values for % lethality, rather than % inhibition

TABLE 4

Ovarian Cancer Targets

| Targets | | | | Assemblies |
|---|---|---|---|---|
| amphiregulin | EGF | ICFI | NOTCH3 | MDM2-p53 |
| BCL-2 | EPHA2* | IL-1 | PDGF | PHOX-BEM1 of PKC |
| BCL-XL | EV11 | IL-6 | PDGFR | CXCR4-CXCL12 |
| BIRCH5 | FGF1 | IL-8 | Pericytes | CD44-hyaluronic acid |
| CA125*# | FGF2 | LPA* | RAB25 | β1 integrin-fibronectin |
| CD44 | FGFR | MDM2 | TGFα | β1 integrin-laminin |
| CXCR4 | heregulin | mesothelin | VEGFA | β1 integrin-Type IV collagen |

*antibodies for these targets available
serum biomarker for ovarian cancer

Example 10. Further Discussion

There are few FDA-approved molecules capable of simultaneous treatment and imaging; one of the most well-known and studied are the tetrapyrrolic macrocycles, which include porphyrins, phthalocyanines, and corroles. These macrocycles are photoactive and their inherent absorbance and emission properties can be exploited for the treatment of diseases, including the porphyrin-based Visudyne used in photodynamic therapy for treatment of macular degeneration. As macrocycles, corroles have significant advantages over other drug classes such as small molecules or biologics; as their large size is on the order needed to target protein-protein interactions and yet they can have unexpectedly high cell permeability. Corroles are typically in the nanometer size regime and interact with macromolecular surfaces, such as those of proteins, and the corrole structure can be modified to increase cellular uptake and nuclear localization, which are traditional challenges for drug candidates. Corroles are inherently fluorescent molecules due to their conjugated π-system, a property that is useful for determining cellular uptake and localization. Recently, we reported two corroles functionalized with carboxylate groups at different ring locations exhibit anticancer activity superior to cisplatin, and unlike porphyrin-related compounds that were used as photosensitizers, corroles do not require photoexcitation to induce cytotoxicity. The ability to access a corrole with a free carboxylate group using mild conditions and biocompatible reagents is tremendously convenient. The carboxylate group is an extremely valuable functional group handle that reacts with free amines in >65% yield, enabling design of and reliable access to modified, functionalized corroles. With the optimized synthetic routes providing greater access to functionalized corroles, demonstrated differentiated cytotoxicity of corroles, and greater understanding of biological targets for specific cancers, there is great potential for corroles to emerge as both cancer therapeutics and diagnostic imaging agents.

Potential Problems and Alternative Strategies

Corrole synthesis, modification and purification can be challenging, however, the development of the corroles exemplified and described herein and the subsequent functionalization with bioorthogonal (e.g., click group) handles (azides, alkynes and strained cyclooctynes) has resulted in two reliable and high-yielding routes for installing targeting groups. Chemical modification of the corrole can be accessed through direct coupling of amines with the desired functionalities to the carboxylated corrole. The work herein has shown the ability to produce such derivatives in isolated yields of 65% or above. Utilization of partner click groups on the corrole framework and a desired targeting group resulted in >90% yield. A wide range of further derivatives is easily envisioned and well within the skill of the person of skill in the art, including reactions attaching antibodies. In such cases, the use of "clickable" corroles will achieve the desired target. For these corrole reaction sequences, each additional step is both more chemo-selective and higher yielding than the previous step.

CONCLUSIONS

Gallium corroles with different ring substituents exhibited variable uptake rates and cytotoxic activity against numerous human cancer cell lines. The uptake, intracellular accumulation, and potency ($IC_{50}$) varied by compound: carboxylated derivatives of Complexes 3 and 4 augmented cell permeability, as revealed by enhanced uptake rates, and increased intracellular accumulation, resulting in higher potency compared with Complexes 1 and 2. The carboxylated corroles exhibited strong cytotoxic effects in prostate, melanoma, breast, and ovarian cancer cells; the effective cytotoxic dose (<20 μM) was lower than that of a widely used chemotherapeutic agent, cisplatin, as well as those of other gallium compounds under study as therapeutic agents. Complex 4 was exceptionally active as a cytotoxic agent against melanoma SK-MEL-28 cells (IC50=4.8 μM); notably, >99% of cells exhibited intracellular corrole accumulation within 15 min. In comparison with 2, Complexes 3 and 4 have lower molecular weights (Mr), smaller polar surface areas (tPSA), and higher calculated lipophilicities (cLogP), all chemical properties associated with enhanced cell permeability and uptake. The carboxylated corroles also displayed high efficacy in cell killing and a highly homogeneous cytotoxic response within each cell population. Because the synthesis of Complex 3, which has anticancer activity close to that of Complex 4, does not require the use of harsh reagents, it represents an easily and safely prepared anticancer lead that also can function as a fluorescence imaging agent.

As those skilled in the art will appreciate, numerous modifications and variations of the present invention are possible in light of these teachings, and all such are contemplated hereby. For example, in addition to the embodiments described herein, the present invention contemplates and claims those inventions resulting from the combination of features of the invention cited herein and those of the cited prior art references which complement the features of the present invention. Similarly, it will be appreciated that any described material, feature, or article may be used in combination with any other material, feature, or article, and such combinations are considered within the scope of this invention.

The disclosures of each patent, patent application, and publication cited or described in this document are hereby incorporated herein by reference, each in its entirety, for all purposes, but at least for the teachings in the context in which the reference is used.

What is claimed:

1. A compound of Formula (I-M):

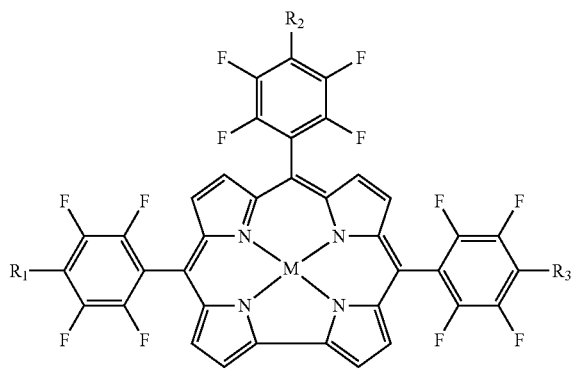

(I-M)

wherein
- $R^1$, $R^2$, and $R^3$ are independently —F or —N(H)—$(CH_2)_m$—Y, provided that at least one of $R^1$, $R^2$, or $R^3$ is —N(H)—$(CH_2)_m$—Y;
- —Y is —$N(Z)_2$, —O—Z, —C(O)—O—Z, —OC(O)Z—, —OC(O)O—Z, —$C(O)N(Z)_2$, —NH—C(O)—Z, —C(O)NHNH—Z
- —Z is independently $R^5$, —$(CH_2)_m$—X, —$(CH_2)_m$—$OR^5$, —$(CH_2)_m$—$SR^5$, —$(CH_2)_m$—$N(R^5)_2$, —$(CH_2CH_2O)_n$—$OR^5$, —$(CH_2CH_2O)_n$—$N(R^5)_2$, —$(CH_2)_m$—$N_3$, —$(CH_2)_m$—C≡C—$R^5$, an amino acid, peptide, protein, polyol;
- $R^5$ is independently H or $C_{1-12}$alkyl;
- X is Cl, Br, or I;
- m is independently 1-18;
- n is 1-32; and
- M is Ag, Al, Co, Cr, Cu, Fe, Ga, Ge, Hf, Ir, Mo, Mn, Nb, Ni, Os, Pt, Re, Rh, Ru, Sb, Sn, Ta, Ti, V, or W, a lanthanide or actinide, or an isotope or radionuclide thereof, each of which is optionally coordinated to one or more ligands.

2. The compound of claim 1, having a Formula (I-M), where M is Al, Cr, Co, Fe, Ga, Mn, Rh, Ru, or Sn having 0, 1, or 2 axial nitrogen donor ligands.

3. The compound of claim 1, having a Formula (I-M), where M is Co, Cr, Fe, Ga, Ir, Mn, Rh, Ru, or Sn having 0, 1, or 2 axial phosphine ligands.

4. The compound of claim 1, having a Formula (I-M), where M is Al or Ga, optionally coordinated to one or more ligands.

5. The compound of claim 1, having a Formula (I-M), where M is Ga(III) having 0, 1, or 2 axial tertiary or aromatic amine ligands.

6. The compound of claim 1, having a Formula (I-M), where M is Ga(III) having 0, 1, or 2 axial pyridine ligands.

7. The compound of any one of claims 1 to 6, wherein two or three of $R^1$, $R^2$, or $R^3$ are —N(H)—$(CH_2)_m$—Y.

8. A pharmaceutical composition comprising a pharmaceutically acceptable inert ingredient and a compound of claim 1.

9. The pharmaceutical composition of claim 8, wherein the composition is in a form suitable for local or systemic administration.

10. The pharmaceutical composition of claim 8 or claim 9 having a Formula (I-M), where M is Al or Ga, optionally coordinated to one or more ligands.

11. The pharmaceutical composition of claim 8 or claim 9, having a Formula (I-M), where M is Ga(III) having 0, 1, or 2 axial tertiary or aromatic amine ligands.

12. The pharmaceutical composition of claim 8 or claim 9, having a Formula (I-M), where M is Ga(III) having 0, 1, or 2 axial pyridine ligands.

13. A method of preparing a compound of claim 1, comprising reacting a compound of Formula (I-H), with a precursor compound or salt of Ag, Al, Co, Cr, Cu, Fe, Ga, Ge, Hf, Ir, Mo, Mn, Nb, Ni, Os, Pt, Re, Rh, Ru, Sb, Sn, Ta, Ti, V, W, a lanthanide or actinide, or an isotope or radionuclide thereof, under conditions to produce a compound of Formula (I-M), so as to produce the compound of Formula (I-M)

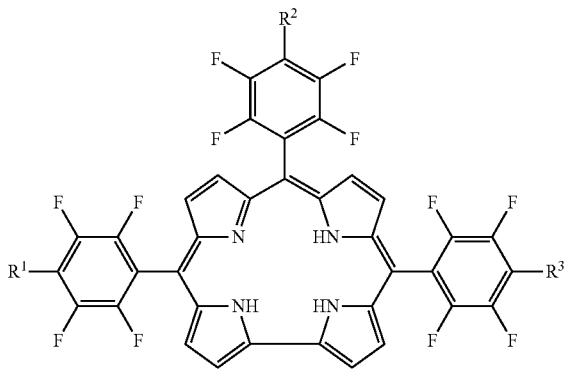

(I-H)

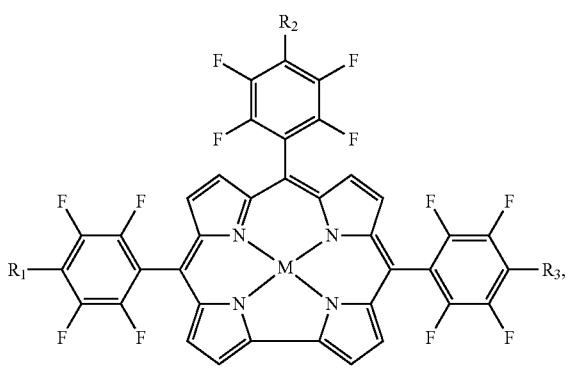

(I-M)

wherein M is Ag, Al, Co, Cr, Cu, Fe, Ga, Ge, Hf, Ir, Mo, Mn, Nb, Ni, Os, Pt, Re, Rh, Ru, Sb, Sn, Ta, Ti, V, W, a lanthanide or actinide, or an isotope or radionuclide thereof, each of which is optionally coordinated to one or more ligands.

14. The compound of claim 1, where M is Ga(III) having one axial pyridine ligand.

15. The pharmaceutical composition of claim 8 or claim 9, where M is Ga(III) having one axial pyridine ligand.

* * * * *